US012533131B1

(12) United States Patent
Bakos et al.

(10) Patent No.: US 12,533,131 B1
(45) Date of Patent: Jan. 27, 2026

(54) MULTI-PART STAPLE WITH SEPARATE LEGS AND CROWN TO FACILITATE STAPLE RELEASE FROM ARBORS

(71) Applicant: Cilag GmbH International, Zug (CH)

(72) Inventors: Gregory J. Bakos, Mason, OH (US); Brian D. Schings, Maineville, OH (US); Nicholas Fanelli, Morrow, OH (US); Jason Rector, Maineville, OH (US)

(73) Assignee: Cilag GmbH International, Zug (CH)

(*) Notice: Subject to any disclaimer, the term of this patent is extended or adjusted under 35 U.S.C. 154(b) by 0 days.

(21) Appl. No.: 18/781,583

(22) Filed: Jul. 23, 2024

(51) Int. Cl.
*A61B 17/072* (2006.01)
*A61B 17/064* (2006.01)

(52) U.S. Cl.
CPC .... *A61B 17/07292* (2013.01); *A61B 17/0643* (2013.01); *A61B 17/07207* (2013.01); *A61B 2017/07271* (2013.01)

(58) Field of Classification Search
CPC .... A61B 17/072; A61B 17/064; A61B 17/068
See application file for complete search history.

(56) References Cited

U.S. PATENT DOCUMENTS

| | | | | |
|---|---|---|---|---|
| 5,205,459 | A | 4/1993 | Brinkerhoff | |
| 8,210,411 | B2 | 7/2012 | Yates et al. | |
| 9,186,142 | B2 | 11/2015 | Fanelli et al. | |
| 9,517,065 | B2 | 12/2016 | Simms et al. | |
| 9,622,746 | B2 | 4/2017 | Simms et al. | |
| 9,717,497 | B2 | 8/2017 | Zerkle et al. | |
| 9,795,379 | B2 | 10/2017 | Leimbach et al. | |
| 9,808,248 | B2 | 11/2017 | Hoffman | |
| 9,839,421 | B2 | 12/2017 | Zerkle et al. | |
| 10,092,292 | B2 | 10/2018 | Boudreaux et al. | |
| 10,182,813 | B2 | 1/2019 | Leimbach et al. | |
| 10,709,452 | B2 | 7/2020 | Dinardo | |
| 10,966,722 | B2 | 4/2021 | Shelton, IV | |
| 11,304,697 | B2 | 4/2022 | Fanelli et al. | |
| 11,317,912 | B2 | 5/2022 | Jenkins et al. | |
| 11,439,391 | B2 | 9/2022 | Bruns et al. | |
| 12,004,744 | B2 | 6/2024 | Schings | |
| 2016/0106427 | A1* | 4/2016 | Shelton, IV | A61B 17/072 227/176.1 |
| 2017/0367699 | A1* | 12/2017 | Shelton, IV | A61B 17/064 |

(Continued)

OTHER PUBLICATIONS

U.S. Appl. No. 63/459,739, filed May 19, 2023.

(Continued)

*Primary Examiner* — Nathaniel C Chukwurah
(74) *Attorney, Agent, or Firm* — Lempia Summerfield Katz LLC

(57) ABSTRACT

A staple cartridge including: a set of arbors disposed adjacent a staple pocket having an opening, the set of arbors including an upper set of arbors and a lower set of arbors; and a multi-part staple including a first staple leg portion, a second staple leg portion, and a crown portion. The crown portion is disposed vertically between the upper set of arbors and the lower set of arbors. The set of arbors are configured to curl the first staple leg portion and the second staple leg portion as the first staple leg portion and the second staple leg portion exit the staple pocket at the opening during a firing stroke.

20 Claims, 22 Drawing Sheets

(56) References Cited

U.S. PATENT DOCUMENTS

| | | | | |
|---|---|---|---|---|
| 2019/0269402 | A1* | 9/2019 | Murray | A61B 17/068 |
| 2019/0328390 | A1* | 10/2019 | Harris | A61B 17/0644 |
| 2020/0038018 | A1* | 2/2020 | Shelton, IV | A61B 17/068 |
| 2023/0301674 | A1 | 9/2023 | Rector | |

OTHER PUBLICATIONS

U.S. Appl. No. 63/467,469, filed May 19, 2023.
U.S. Appl. No. 63/467,615, filed May 19, 2023.
U.S. Appl. No. 63/467,622, filed May 19, 2023.
U.S. Appl. No. 63/467,623, filed May 19, 2023.
U.S. Appl. No. 63/467,648, filed May 19, 2023.
U.S. Appl. No. 63/467,656, filed May 19, 2023.

* cited by examiner

MULTI-PART STAPLE WITH SEPARATE LEGS AND CROWN TO FACILITATE STAPLE RELEASE FROM ARBORS

BACKGROUND

Open surgery (e.g., traditional surgery, conventional surgery, open or non-endoscopic procedures, and the like) involves creating a single large incision in the body to access the affected area. During open surgery, a surgeon may work directly with their hands and may have a broader view of the surgical site. In some instances, such as in the case of transplants, large incisions are necessary to remove the damaged organ and replace it with a healthy one. This type of surgery is also used in a variety of treatments, such as the removal of kidney stones.

Surgical staplers are frequently used in surgical procedures for suturing body tissues such as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. During the typical suturing process, pusher members associated with the cartridge are controllably advanced by the operating mechanism of the instrument in a manner to urge the staples out of the cartridge, through the tissue and forcibly against the anvil.

More particularly, surgical staplers, also referred to as endocutters or stapler cutters, typically include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of wedges which, when driven distally, pass through openings in the staple cartridge and engage drivers supporting the staples to affect the firing of the staples toward the anvil.

One such frequently used type of surgical stapler is the open linear stapler, which is a device that enables the surgeon to simultaneously place one or more rows of surgical staples in body tissue or organs. By way of example, a typical procedure is a pneumonectomy, which is a removal of a portion of the patient's lungs. The linear stapler can be used several times during this procedure, including for the occlusion of the pulmonary artery prior to its resection. For this later use, the surgeon first clamps the jaws of the stapler across the artery, then forms the staple and before reopening the stapler jaws, cuts the artery with a scalpel using the edge of the staple jaws as a guide.

In some settings, endoscopic or laparoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path.

It may be desirable to sever and staple tissue of various thicknesses. A thin layer of tissue may result in staples that only form loosely, perhaps requiring the need for bolstering material. A thick layer of tissue may result in formed staples that exert a strong compressive force on the captured tissue, perhaps resulting in necrosis, bleeding or poor staple formation/retention. Rather than limiting the range of tissue thicknesses that are appropriate for a given surgical stapling and severing instrument, it would be desirable to accommodate a wider range of tissue thickness with the same surgical stapling and severing instrument.

In certain types of surgical procedures the use of surgical staples has become the preferred method of joining tissue, and, specially configured surgical staplers have been developed for these applications. For example, intra-luminal or circular staplers have been developed for use in a surgical procedure known as an anastomosis. Circular staplers useful to perform an anastomosis are disclosed, for example, in U.S. Pat. Nos. 5,205,459 and 10,709,452 which are each herein incorporated by reference.

Staple forming requires high loads to initiate buckling of the staple legs, particularly when the staple legs buckle multiple times, and a very high load is typically generated when firing in a traditional way against staple forming pockets of an anvil. These high loads may result in poorly formed staples and high firing loads. Curling staple legs using staple forming anvil pockets also requires precise anvil pocket alignment in order to properly form the staples. Further, staple formation using staple forming pockets on the anvil may be negatively impacted by tissue conditions or misalignment between staples and pockets, which also may lead to poorly formed staples.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIGS. 21A and 22B depict deforming apertures within a pledget according to one embodiment.

Figure 1:
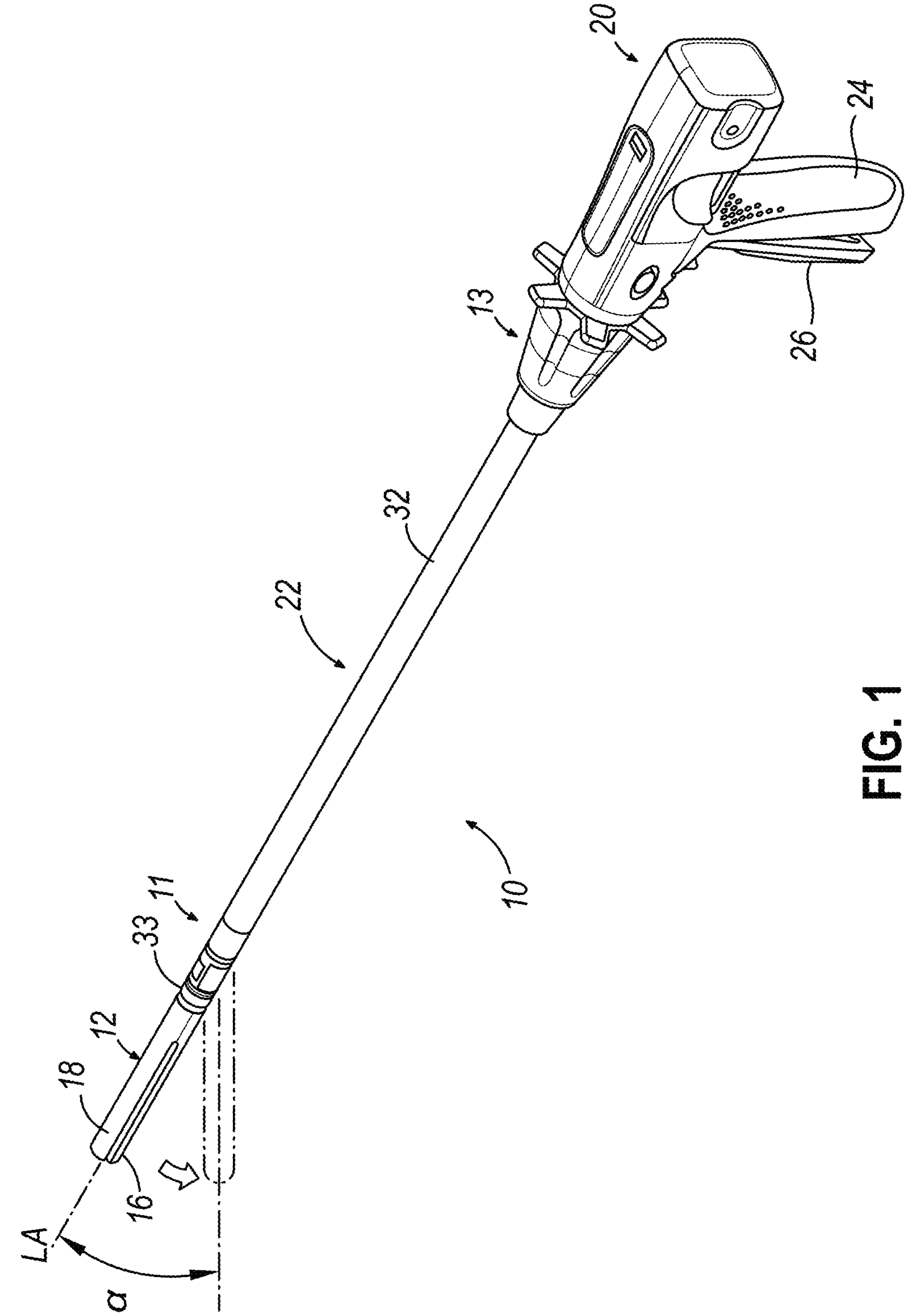
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

Applicant of the present application also owns the following U.S. Patent Applications that were filed on Jul. 23, 2024 and which are each herein incorporated by reference in their respective entireties:

U.S. patent application Ser. No. 18/781,545, entitled "Method For Pre-Bending Staple Tips Using An Arbor Plate,"

U.S. patent application Ser. No. 18/781,551, entitled "Staple Cartridge Containing Forming Surfaces That Bend Staple Legs Upon Exiting,";

U.S. patent application Ser. No. 18/781,555, entitled "Stapler Device That Forms Staples From Various Cartridges Having Different Row Patterns,";

U.S. patent application Ser. No. 18/781,558, entitled "Staple Shape Control Using Selective Bending Segments Of Staples,";

U.S. patent application Ser. No. 18/781,566, entitled "Staple Cartridge With Static Angled Arbors To Form Three-Dimensional (3D) Staples,";

U.S. patent application Ser. No. 18/781,573, entitled "Staple Cartridge With Dynamic Arbors That Produce Non-Constant Curl Radius,"; and U.S. patent application Ser. No. 18/781,578, entitled "Deployable Arbor Sets That Break Away From Staple Cartridge."

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

Spatial and functional relationships between elements are described using various terms, including "connected," "engaged," "interfaced," "on," and "coupled." Unless explicitly described as being "direct," when a relationship between first and second elements is described in the present disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, on, or coupled to another element, there are no intervening elements present. Other words used to describe the relationship between elements should be interpreted in a like fashion (e.g., "between," versus "directly between," "adjacent," versus "directly adjacent," and the like.).

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Staplers

FIGS. 1-7 depict an example of a surgical stapling and severing instrument 10 that is sized for insertion through a trocar cannula or an incision (e.g., thoracotomy, etc.) to a surgical site in a patient for performing a surgical procedure. Instrument 10 of the present example includes a handle portion 20 connected to a shaft 22, which distally terminates in an articulation joint 11, which is further coupled with an end effector 12. Once articulation joint 11 and end effector 12 are inserted through the cannula passageway of a trocar, articulation joint 11 may be remotely articulated, as depicted in phantom in FIG. 1, by an articulation control 13, such that end effector 12 may be deflected from the longitudinal axis (LA) of shaft 22 at a desired angle (a). End effector 12 of the present example includes a lower jaw 16 (also referred to herein as a cartridge jaw) that includes a staple cartridge 37, and an upper jaw in the form of a pivotable anvil jaw 18.

Unless otherwise described, the term "pivot" (and variations thereof) as used herein encompasses but is not necessarily limited to pivotal movement about a fixed axis. For instance, in some versions, anvil jaw 18 may pivot about an axis that is defined by a pin (or similar feature) that slidably translates along an elongated slot or channel as anvil jaw 18 moves toward lower jaw 16. Such translation may occur before, during, or after the pivotal motion. It should therefore be understood that such combinations of pivotal and translational movement are encompassed by the term "pivot" and variations thereof as used herein.

Handle portion 20 includes a pistol grip 24 and a closure trigger 26. Closure trigger 26 is pivotable toward pistol grip 24 to cause clamping, or closing, of anvil jaw 18 toward lower jaw 16 of end effector 12. Such closing of anvil jaw 18 is provided through a closure tube 32 and a closure ring 33, which both longitudinally translate relative to handle portion 20 in response to pivoting of closure trigger 26 relative to pistol grip 24. Closure tube 32 extends along the length of shaft 22; and closure ring 33 is positioned distal to articulation joint 11. Articulation joint 11 is operable to communicate/transmit longitudinal movement from closure tube 32 to closure ring 33.

Figure 2:
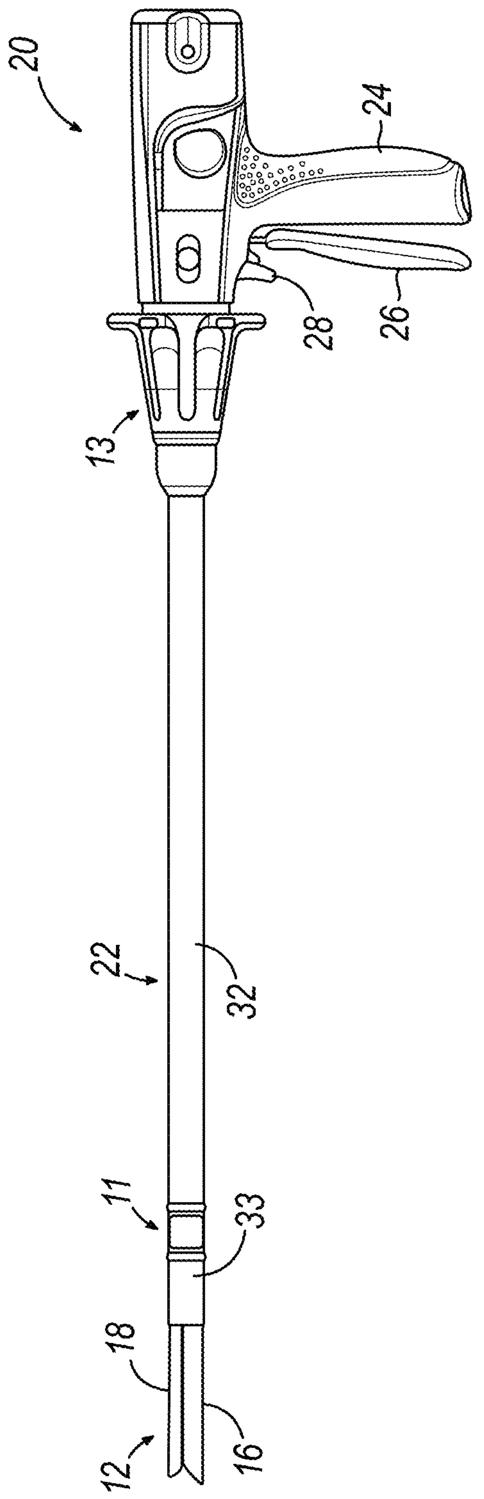
FIG. 2 depicts a side view of the instrument of FIG. 1.

As shown in FIG. 2, handle portion 20 also includes a firing trigger 28. An elongate member (not shown) longitudinally extends through shaft 22 and communicates a longitudinal firing motion from handle portion 20 to a firing beam 14 in response to actuation of firing trigger 28. This distal translation of firing beam 14 causes the stapling and severing of clamped tissue in end effector 12, as will be described in greater detail below.

FIGS. 3-6 depict end effector 12 employing an E-beam form of firing beam 14 to perform a number of functions. It should be understood that an E-beam form is just a merely illustrative example. Firing beam 14 may take any other suitable form, including but not limited to non-E-beam forms. As shown in FIGS. 3-6, end effector 12 employs a firing beam 14 that includes a transversely oriented upper pin 38, a firing beam cap 44, a transversely oriented middle pin 46, and a distally presented cutting edge 48. Upper pin 38 is positioned and translatable within a longitudinal anvil slot 42 of anvil jaw 18. Firing beam cap 44 slidably engages a lower surface of lower jaw 16 by having firing beam 14 extend through lower jaw slot 45 (shown in FIG. 4B) that is formed through lower jaw 16. Middle pin 46 slidingly engages a top surface of lower jaw 16, cooperating with firing beam cap 44. Thereby, firing beam 14 affirmatively spaces end effector 12 during firing.

Some non-E-beam forms of firing beam 14 may lack upper pin 38, middle pin 46 and/or firing beam cap 44. Some such versions of instrument 10 may simply rely on closure ring 33 or some other feature to pivot anvil 18 to a closed position and hold anvil 18 in the closed position while firing beam 14 advances to the distal position. Other suitable forms that firing beam 14 may take should be apparent to those of ordinary skill in the art in view of the teachings herein.

Figure 3:
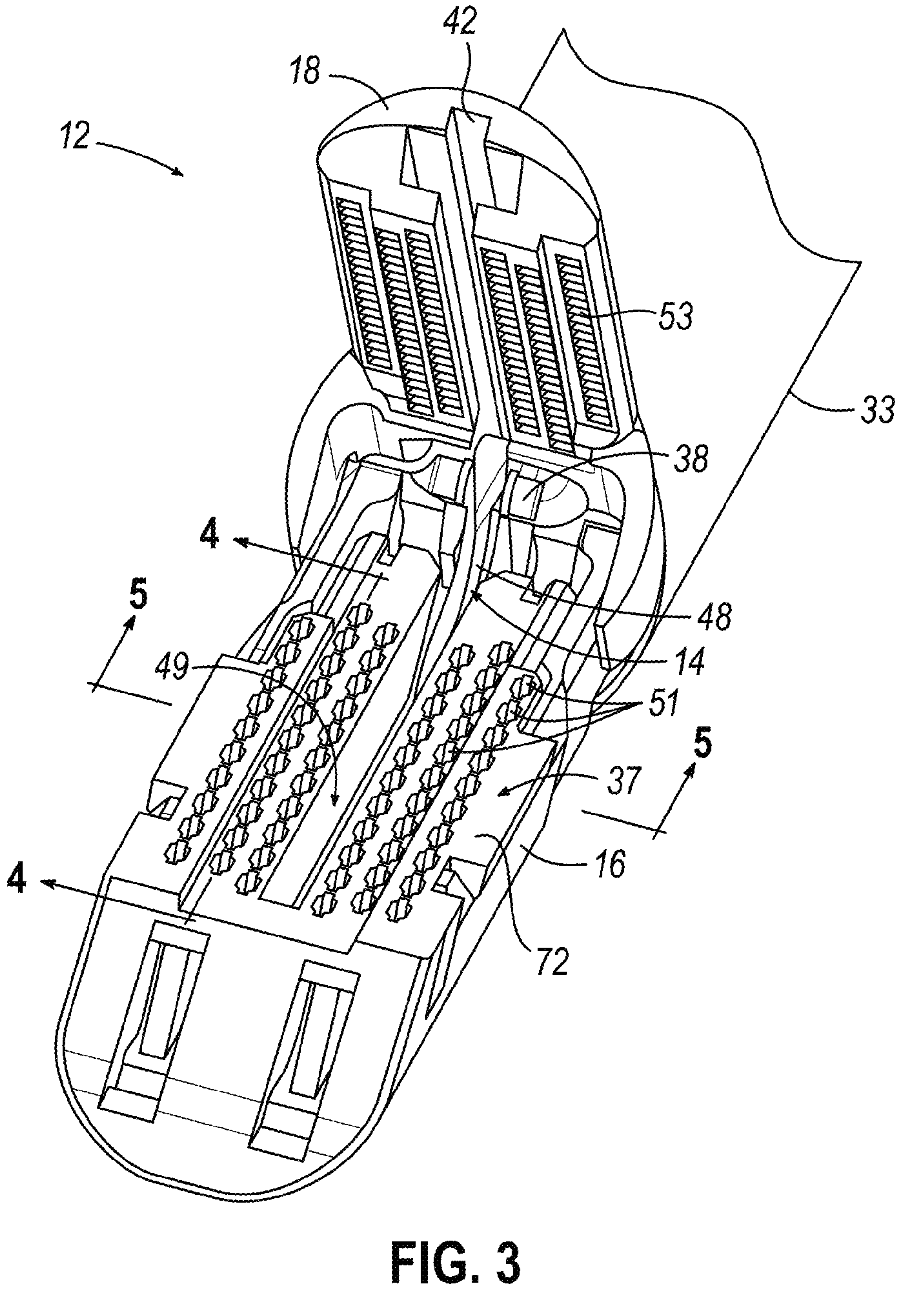
FIG. 3 depicts a perspective view of an opened end effector of the instrument of FIG. 1.
Figure 4A:
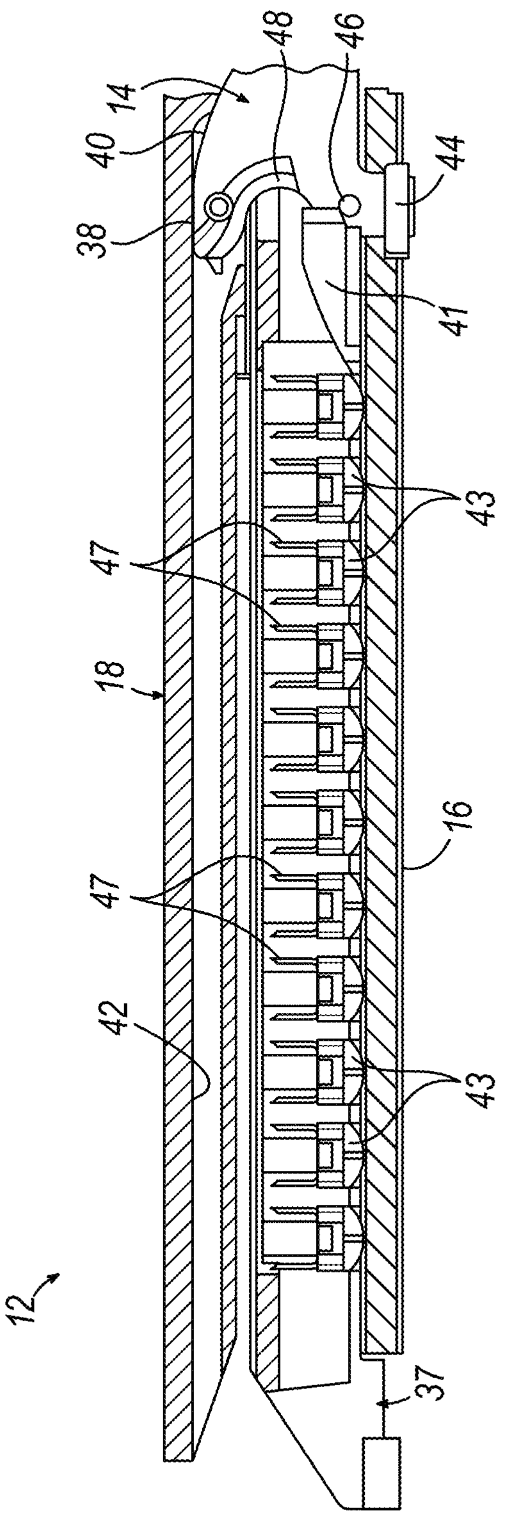
FIG. 4A depicts a side cross-sectional view of the end effector of FIG. 3, taken along line 4-4 of FIG. 3, with the firing beam in a proximal position.
Figure 4B:
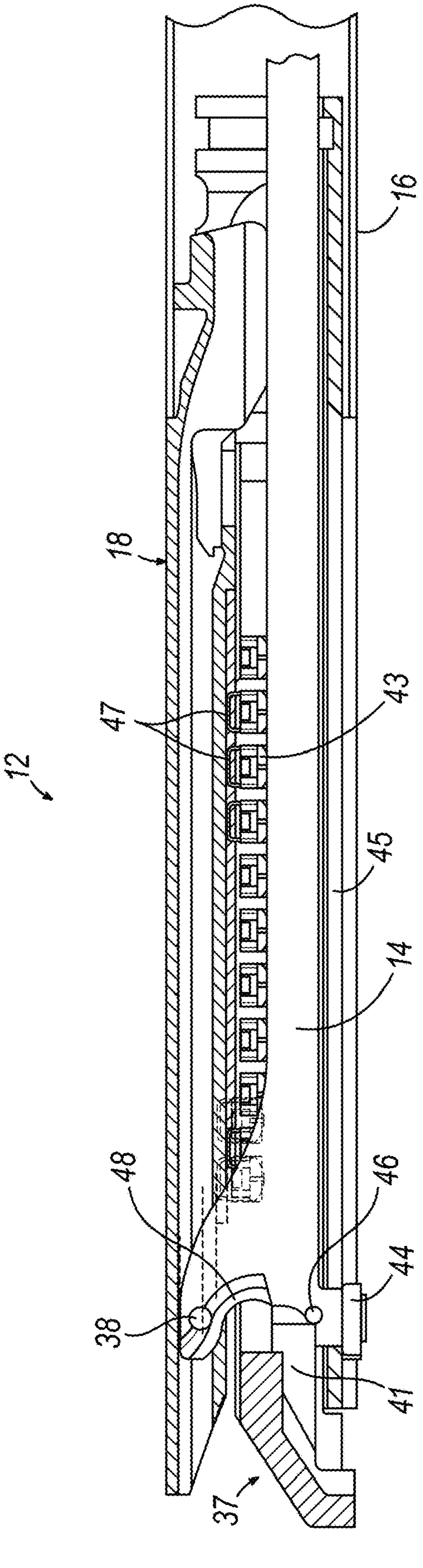
FIG. 4B depicts a side cross-sectional view of the end effector of FIG. 3, taken along line 4-4 of FIG. 3, with the firing beam in a distal position.
Figure 5:
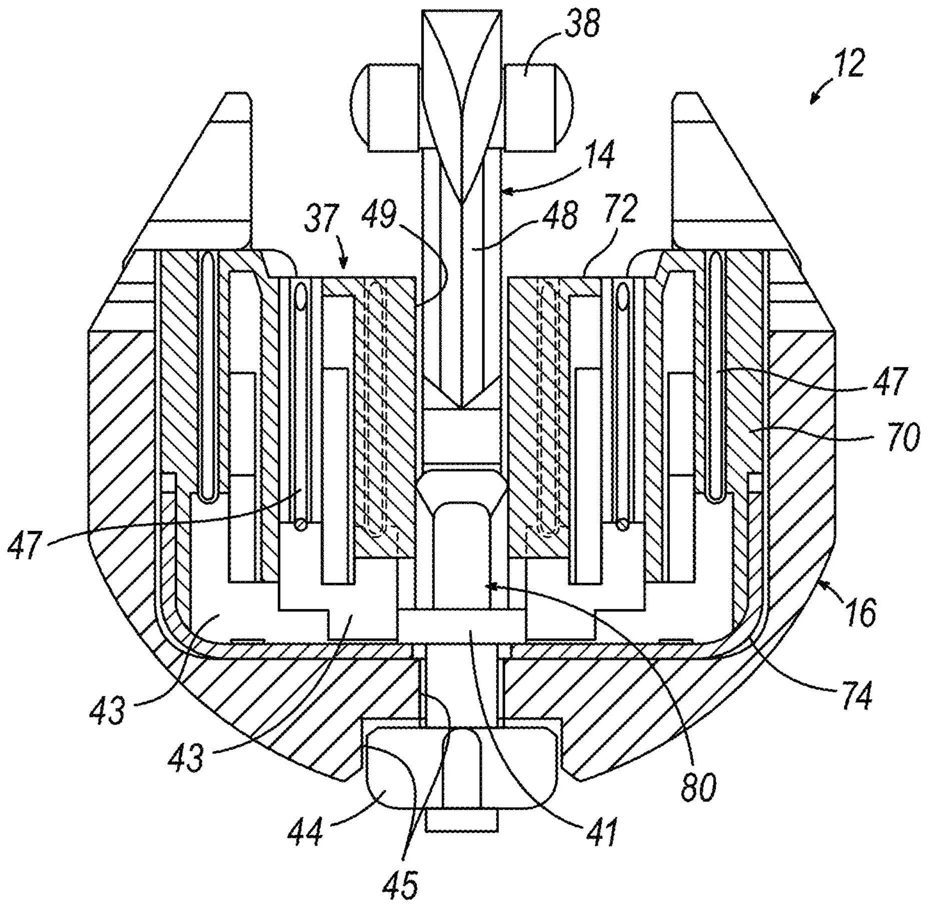
FIG. 5 depicts an end cross-sectional view of the end effector of FIG. 3, taken along line 5-5 of FIG. 3.
Figure 6:
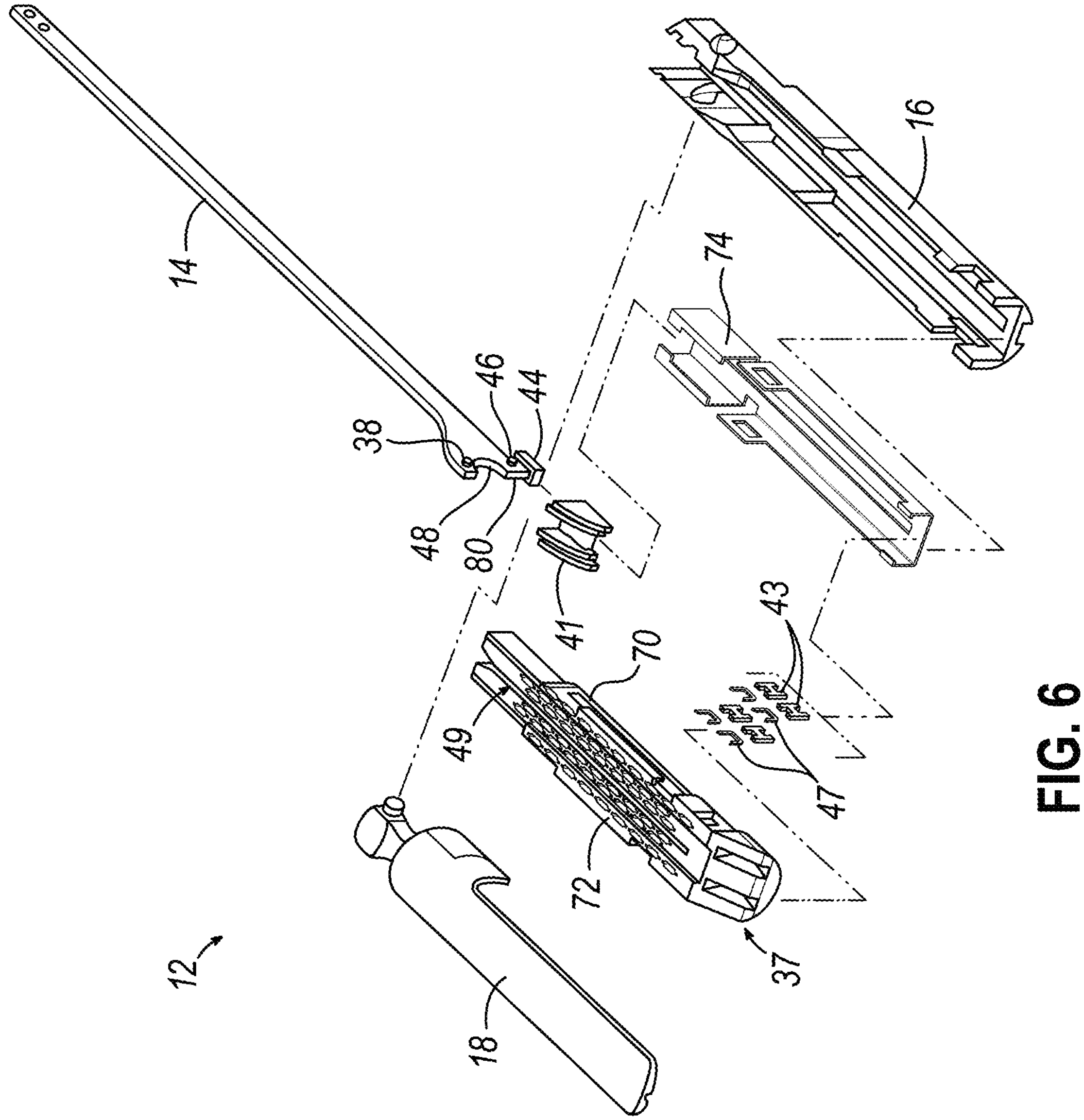
FIG. 6 depicts an exploded perspective view of the end effector of FIG. 3.

FIG. 3 shows firing beam 14 of the present example proximally positioned and anvil jaw 18 pivoted to an open configuration, allowing an unspent staple cartridge 37 to be removably installed into a channel of lower jaw 16. As best seen in FIGS. 5-6, staple cartridge 37 of the present example includes a cartridge body 70, which presents an upper deck 72 and is coupled with a lower cartridge tray 74. As best seen in FIG. 3, a vertical slot 49 extends longitudinally through a portion of staple cartridge body 70. As also best seen in FIG. 3, three rows of staple apertures 51 are formed through upper deck 72 on each lateral side of vertical slot 49. As shown in FIGS. 4A-6, a wedge sled 41 and a plurality of staple drivers 43 are captured between cartridge body 70 and tray 74, with wedge sled 41 being located proximal to staple drivers 43. Wedge sled 41 is movable longitudinally within staple cartridge 37; while staple drivers 43 are movable vertically within staple cartridge 37. Staples 47 are also positioned within cartridge body 70, above corresponding staple drivers 43. Each staple 47 is driven vertically within cartridge body 70 by a staple driver 43 to drive staple 47 out through an associated staple aperture 51. As best seen in FIGS. 4A-4B and 6, wedge sled 41 presents inclined cam surfaces that urge staple drivers 43 upwardly as wedge sled 41 is driven distally through staple cartridge 37.

With end effector 12 closed, as depicted in FIGS. 4A-4B by distally advancing closure tube 32 and closure ring 33, a firing member in the form of firing beam 14 is then advanced distally into engagement with anvil jaw 18 by having upper pin 38 enter longitudinal anvil slot 42. A pusher block 80

(shown in FIG. 5) located at distal end of firing beam 14 pushes wedge sled 41 distally as firing beam 14 is advanced distally through staple cartridge 37 when firing trigger 28 is actuated. During such firing, cutting edge 48 of firing beam 14 enters vertical slot 49 of staple cartridge 37, severing tissue clamped between staple cartridge 37 and anvil jaw 18. As shown in FIGS. 4A-4B, middle pin 46 and pusher block 80 together actuate staple cartridge 37 by entering into vertical slot 49 within staple cartridge 37, driving wedge sled 41 into upward camming contact with staple drivers 43, which in turn drives staples 47 out through staple apertures 51 and into forming contact with staple forming pockets 53 (shown in FIG. 3) on inner surface of anvil jaw 18. FIG. 4B depicts firing beam 14 fully distally translated after completing severing and stapling of tissue. Staple forming pockets 53 are intentionally omitted from the view in FIGS. 4A-4B but are shown in FIG. 3. Anvil jaw 18 is intentionally omitted from the view in FIG. 5.

Figure 7:
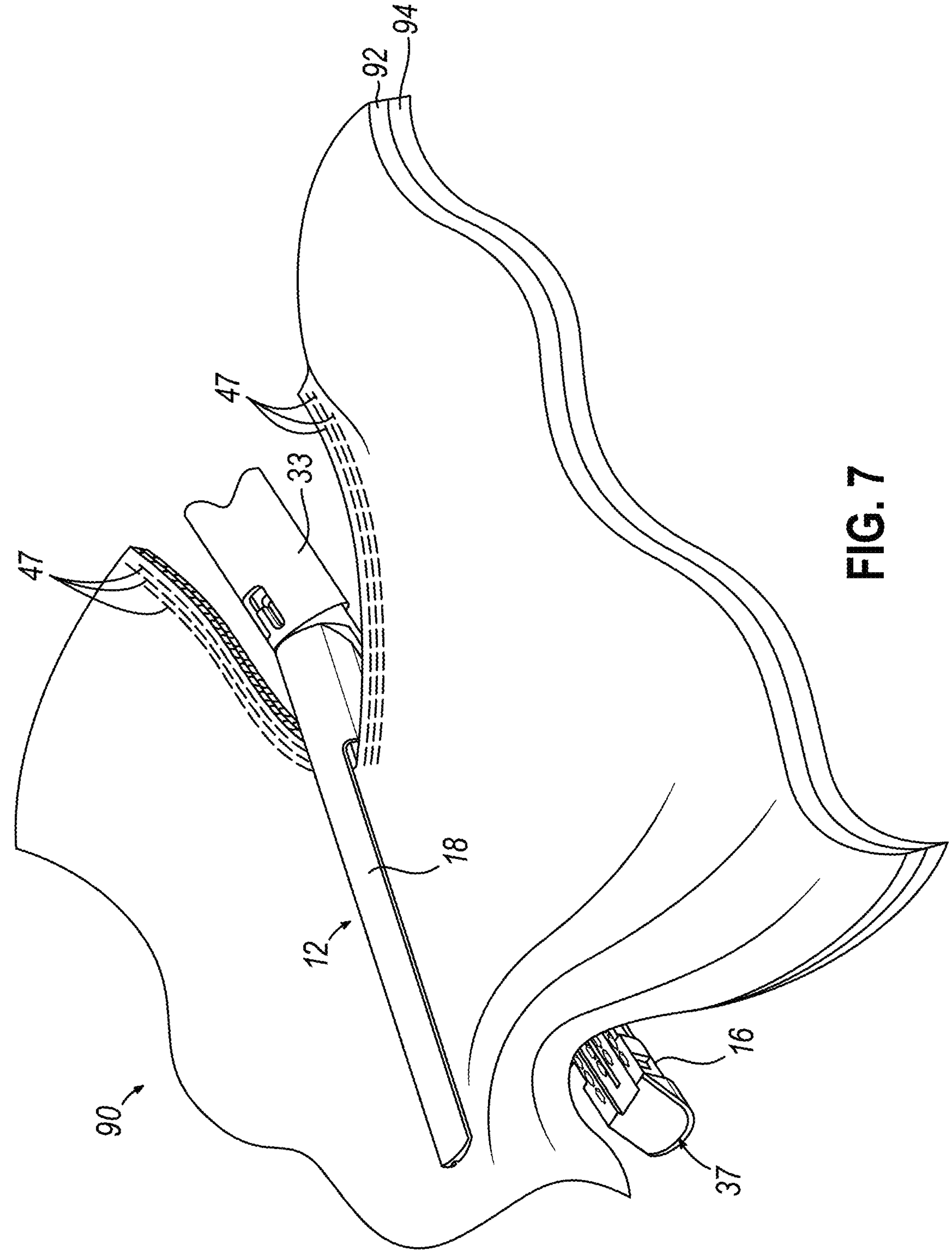
FIG. 7 depicts a perspective view of the end effector of FIG. 3, positioned at tissue and having been actuated once in the tissue.

FIG. 7 shows end effector 12 having been actuated through a single firing stroke through tissue 90. Cutting edge 48 (obscured in FIG. 7) has cut through tissue 90, while staple drivers 43 have driven three alternating rows of staples 47 through tissue 90 on each side of the cut line produced by cutting edge 48. After the first firing stroke is complete, end effector 12 is withdrawn from the patient, spent staple cartridge 37 is replaced with a new staple cartridge 37, and end effector 12 is then again inserted into the patient to reach the stapling site for further cutting and stapling. This process may be repeated until the desired quantity and pattern of firing strokes across the tissue 90 has been completed.

It should be understood that cutting edge 48 may sever tissue substantially contemporaneously with staples 47 being driven through tissue during each actuation stroke. In the present example, cutting edge 48 just slightly lags behind driving of staples 47, such that a staple 47 is driven through the tissue just before cutting edge 48 passes through the same region of tissue, though it should be understood that this order may be reversed or that cutting edge 48 may be directly synchronized with adjacent staples. While FIG. 7 shows end effector 12 being actuated in two layers 92, 94 of tissue 90, it should be understood that end effector 12 may be actuated through a single layer of tissue 90 or more than two layers 92, 94 of tissue. It should also be understood that the formation and positioning of staples 47 adjacent to the cut line produced by cutting edge 48 may substantially seal the tissue at the cut line, thereby reducing or preventing bleeding and/or leaking of other bodily fluids at the cut line. Furthermore, while FIG. 7 shows end effector 12 being actuated in two substantially flat, apposed planar layers 92, 94 of tissue, it should be understood that end effector 12 may also be actuated across a tubular structure such as a blood vessel, a section of the gastrointestinal tract, etc. FIG. 7 should therefore not be viewed as demonstrating any limitation on the contemplated uses for end effector 12. Various suitable settings and procedures in which instrument 10 may be used should be apparent to those of ordinary skill in the art in view of the teachings herein.

Instrument 10 may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

Figure 8:
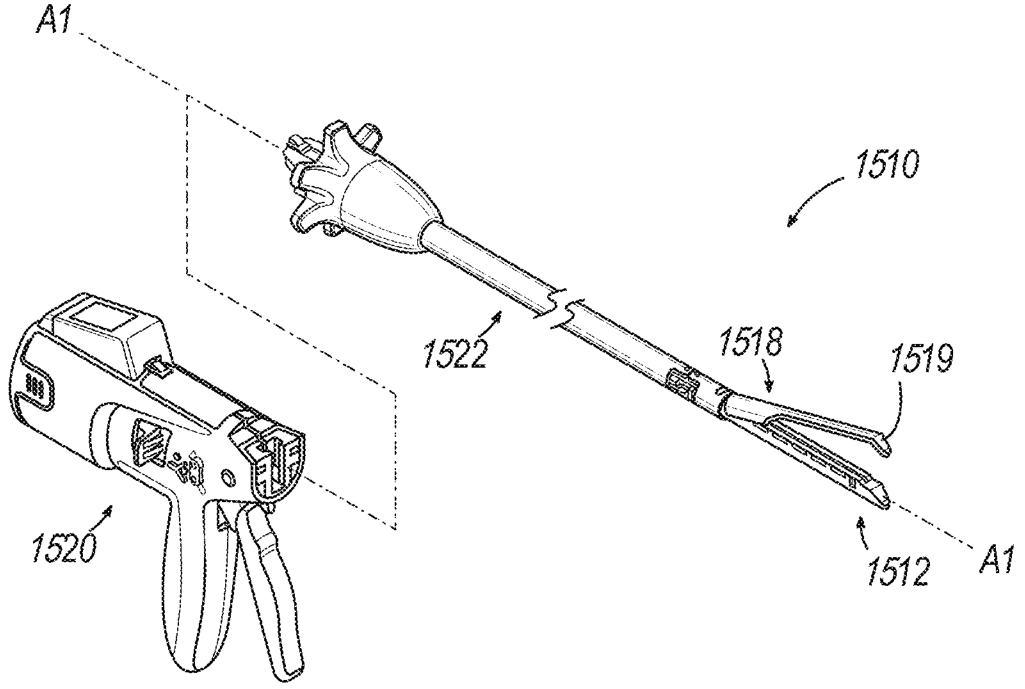
FIG. 8 depicts a perspective view of an example of a surgical stapling instrument having a modular end effector.

FIG. 8 shows another example of an instrument 1510 configured as a surgical stapler. Instrument 1510 includes a handle portion 1520 and a shaft 1522. Instrument 1510 has a modular configuration such that shaft 1522 is selectively removable from, and attachable to, handle portion 1520. Instrument 1510 is configured similarly to instrument 10 such that the operability and use of instrument 1510 is the same as described above for instrument 10 with the added feature of instrument 1510 being a modular configuration. With its modular configuration, instrument 1510 provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument 1510 may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument 1510 with a modular configuration will be apparent to those of ordinary skill in the art in view of the teachings herein. Moreover, it will be understood by those of ordinary skill in the art in view of the teachings herein, that instrument 10 may be modified to incorporate a modular configuration as shown and described with respect to instrument 1510 or other instruments incorporated by reference herein.

It will be appreciated that end effector 1512 may be used in place of end effector 12 shown in FIG. 1. In some versions, end effector 1512 may be integrally formed with shaft 1522 or alternatively may be separately formed and then combined. In some versions, end effector 1512 may be provided for use in robotic systems. In such robotic systems, modular shaft 1522 having end effector 1512 may be attachable to a portion of the robotic system for use such that handle portion 1520 is replaced by components of the robotic system. Still in other examples, end effector 1512 may be adapted for use with a robotic system in a manner where end effector 1512 connects with the robotic system without necessarily connecting the entire modular shaft 1522. In view of the teachings herein, other ways to incorporate an end effector into a user operated or robotic operated instrument will be apparent to those of ordinary skill in the art.

II. Staple Cartridge Containing Forming Surfaces that Bend Staple Legs Upon Exiting Proper staple formation is important in all types of surgical staplers. If the grasped tissue is thicker than can be successfully accommodated by the staple height, the formation of the staple (referred to as the "b-form") may be too tight or small, which may cut off blood supply resulting in necrosis. If the grasped tissue is thinner than can be successfully stapled due to the staple height being too tall or wide, the formed staples may not be able to apply sufficient compression to effectively seal the tissue resulting in bleeding or oozing.

There are a number of areas for improvement regarding the staple forming process. As mentioned above, conventional staple forming technologies involve a pair of cooperating jaw members, where one of the jaw members receives a staple cartridge having rows of staples and the other jaw member defines an anvil having staple forming pockets aligned with the rows of staples in the cartridge. As the staples are driven upwards out of the staple channel (e.g., cavities or pockets) and into tissue by staple drivers and wedge sleds, the tips of the staple legs engage the surfaces of associated staple forming pockets of the anvil, which causes the staple legs to curl (i.e., bend or buckle), ultimately resulting in bent/formed staples.

Staple buckling against the anvil on the other side of tissue requires a high load and impacts the required force to fire the stapler. Generally, staple buckling against the anvil results in one or more peaks of a load profile for firing the stapler. As soon as a staple contacts the staple forming pocket of the anvil, a first peak of firing force occurs, since a higher force is necessary to buckle the staple against the anvil. Once the initial buckling happens, the tip of the staple may scrape along the staple forming pocket and the staple might experience a second bend or buckle, which imparts a second peak of firing force. Reducing the buckling of the staple, or the number of times the staple buckles, would significantly reduce the total amount of force required to fire a surgical stapler. Further, another problem with buckling against an anvil is that force of the staple being pushed against the anvil acts to separate the jaws of the surgical stapler. Curling staples without buckling against the anvil would alleviate this problem.

In order to achieve proper staple formation with the above approach (i.e., buckling against staple forming pockets of the anvil), the alignment between the staples in the staple channels/openings/cavities/pockets of the staple cartridge and the associated staple forming pockets of the anvil must be precise. Misalignment may result in improper staple formation, which may cause poor hemostasis, trauma on layers of tissue (e.g., tearing of tissue), or insufficient compression that leads to bleeding or oozing. Precise alignment requires very small tolerance ranges (e.g., thousandths of an inch), which makes manufacturing cartridges and associated anvils within these tolerance ranges rather difficult.

Another problem with having to match the staple pocket pattern of the staple cartridge with the staple forming pocket pattern of the anvil is that only one type of staple cartridge may be used with any given anvil of a particular pocket pattern. Using different staple cartridges with the same anvil (or swapping out with different anvils) currently requires complex modularity or adapters. In other words, currently, a same or similar staple pattern of a staple cartridge of conventional technology requires the use of the same anvil (i.e., the anvil having the same anvil pocket configuration) and a different staple pattern requires the use of a different anvil (i.e., an anvil having a different anvil pocket configuration).

Therefore, it would be beneficial to control staple forming without relying on staple forming pockets of the anvil. An anvil without staple forming pockets would be simpler and more economical to manufacture. A flat plated anvil, or an anvil with one or more simple troughs or clearance pockets, would also overcome the tolerance and alignment issues described above. In other words, even if a flat plate upper jaw (as opposed to a conventional anvil) that is used to hold the tissue in place happens to also deflect staple tips to assist with staple forming, the specific alignment previously required is not needed. Having a "universal" upper jaw or anvil without specific staple forming pockets would also allow a single stapler to be able to fire with all different types of cartridge reloads, minimizing the need for complex modularity or adapters as well as reload-to-gun lockouts (i.e., safety mechanisms that prevent a wrong cartridge type from being fired with a mismatched anvil), which is very beneficial.

The proposed cartridge designs described herein forms staples without buckling against a distant anvil on other side of tissue grasped between jaws of an end effector. Staple legs are plastically bent (i.e., curled) as they exit the cartridge, using features joined to the cartridge itself. This eliminates the need for pocket alignment, reduces force to fire since buckling is being reduced or eliminated, and provides high control of forming features because they are less impacted by tissue conditions. The proposed designs can allow for various types of cartridge reloads to be fired from the same surgical tool, eliminating the need for modularity. The proposed designs can also be embodied in all of endocutters as well as circular, curved, open, and linear staplers to reduce the need for anvil alignment, and compensate for deflection.

Spring forming machines bend shapes in wire fed by rollers, and around a movable set of arbors. The present disclosure applies that approach to a surgical stapler to form wire that captures tissue without buckling against a distant anvil. The wire can be a leg of a staple, the feeding occurs from the lifting of the driver, and the arbors are new features added at exit locations of cartridge pockets. The present disclosure thus provides staple cartridges with arbors at or near the cartridge deck and/or the tissue gripping features of staple cartridges (or in some cases a separate arbor plate disposed on top of the cartridge), where the arbors curl the staple legs as a driver lifts a staple out of the cartridge channel, in many cases without buckling or deflecting against an anvil. These features, or arbors, at or near the exit of staple pockets allow for improved control over the curl of staple legs and thus staple forming.

As used herein, the term "arbor" may refer to a short bar, shaft, stem, beam, spindle, guide, rod, post, or pin, or other deflection protrusion or wire (e.g., staple leg) bending or curling surface. In some examples, an "arbor" may act as a mandrel, such as a cylindrical rod around which metal (e.g., staple leg) is formed or shaped. In some examples, an "arbor" may be integrally formed as part of a cartridge channel, such as a protrusion of a sidewall of a cartridge channel, or staple driver, or other stapler component. In yet other examples, an "arbor" may be a separate and distinct component that is capable of being removed without destroying the integrity of the other stapler components. In some examples, "arbors" may be part of the staple cartridge deck, be part other features located on the cartridge deck (e.g., tissue gripping features or gripping surface technologies), or be part of an arbor plate configured to be disposed on top of staple cartridges or decks. In each case, the arbors are configured to interact with the staple (e.g., staple legs) as the staple exits the staple pockets of the staple cartridge.

Using the proposed designs described herein, tolerances that control the staple shape are controlled in manufacturing of the cartridge (or arbor plate) component only, since the anvil can be made without staple forming anvil pockets and simply be used to hold tissue against the staple cartridge.

This eliminates the need for the strict pocket alignment described above. Once tolerances are satisfied for a particular cartridge or arbor plate design, variables are set and the cartridges/plates can be manufactured. The proposed cartridge designs impart force to fire advantages as well. For example, the curling load is resolved in one jaw—the cartridge jaw—and not across movable jaws. Further, the continuous bending of the staple wire is more controlled and requires a lower load than buckling short segments as previously done. In other words, continuous staple bending provides a lower steady load value as compared to multiple buckling peak load values of conventional staple forming methods, since after the initial bending load the load value required to finish the firing plateaus. Further, with curling staples as soon as the staple leaves the cartridge, the reduced or eliminated impact against the anvil also reduces or eliminates the force acting to separate the jaws. Pre-curling or pre-bending the staples also provides the ability to have staple formations tighter than the distance between jaws, since the tips of the staples may not need to extend through the tissue to reach the anvil in order to curl/bend. Correct positioning of the proposed staple forming features, or arbors, described herein also allows for positive retention of staples in the staple cartridges without the need for a separate cover or cap, particularly for non-titanium staples that may have less natural spring force.

In one embodiment, the wire bending (e.g., curling) or staple forming surfaces, such as arbors, may be fixed and disposed on an inner wall or surface of a staple cartridge pocket or opening (i.e., part of the staple cartridge body). The arbors may be positioned at or near the exit of the cartridge pocket (also referred to as a staple pocket, staple channel, or staple cavity) such that the staple legs of a staple are curled by the arbors as the staple legs exit the staple pocket. In an embodiment, there are at least two arbors or staple forming surfaces located at the exit of the staple pocket for each staple leg, such that one staple forming surface is on each side of the staple leg being bent. As mentioned above, the staple forming surfaces may be fixed during the formation of the staple (i.e., during the curling of the staple legs as the staple legs exit the staple pocket of the staple cartridge body).

In some embodiments, one or more of the arbors or staple forming surfaces may be movable, releasable or detachable. For example, the arbors or staple forming surfaces may be released with the fully curled staple legs after the staple forming is complete. In this case, the arbors may be made out of a bioabsorbable material. In another example, the staple cartridge may contain a mechanism or device that retracts the arbors. In other words, the arbors may be moved out of the way to allow the staples to deploy or exit the cartridge pocket. In yet another example, the arbors or staple forming surfaces may be designed to allow the staple crown to pass through the arbors or staple forming surfaces. Thus, the staple cartridges described here may use arbors or staple forming surfaces of the types described in U.S. patent application Ser. No. 18/781,578, entitled “Deployable Arbor Sets That Break Away From Staple Cartridge,” the disclosure of which is incorporated by reference herein, in its entirety.

In one embodiment, the staple forming surfaces or arbors may be simple round pins placed at the exit of a staple cartridge pocket. These pins may be wires, posts, pins, and the like with a diameter of up to one and a half times (1.5×) the diameter of the staple wire. This size constraint is practical in space between jaws of a surgical stapler, either linear, laparoscopic, circular, or curved, so that there is an appropriate gap between opposing jaws of a surgical stapler. In another embodiment, the staple forming surfaces may be a protrusion on an inner surface or wall of the staple pocket, such as a rounded surface protrusion, as described below.

The staple shape and leg angle moving through and against the arbors controls the bending radius of the staple legs as they are advanced past or through the arbors. As the staple is raised and the crown approaches the arbors, the staple leg curl radius can change and tighten so that it gathers and then compresses tissue after the tips of the staple legs reach the top plate (opposite jaw), which has no pocket features, as mentioned above. The curvature of the staple wire may be set based on expected tissue thickness to be captured between opposing jaws. The staple wire curvature may also be set to fully cover the tissue gap to the opposing jaw so that all of the tissue is captured and fastened by the formed staple.

The arbors or staple forming surfaces described herein may be used with many different types of staples, including staples where the staple legs extend upwardly from the staple crown in a substantially straight and parallel manner, staples where the staple legs include different segments of varying length and angles at which those segments extend away from each other, as well as staples having angles in two planes.

The disclosed arbors or staple forming surfaces thus allow for the forming of staples without the need for a staple forming pocket on an anvil jaw opposite the cartridge jaw (i.e., the jaw containing or holding the staple cartridge).

Figure 9:
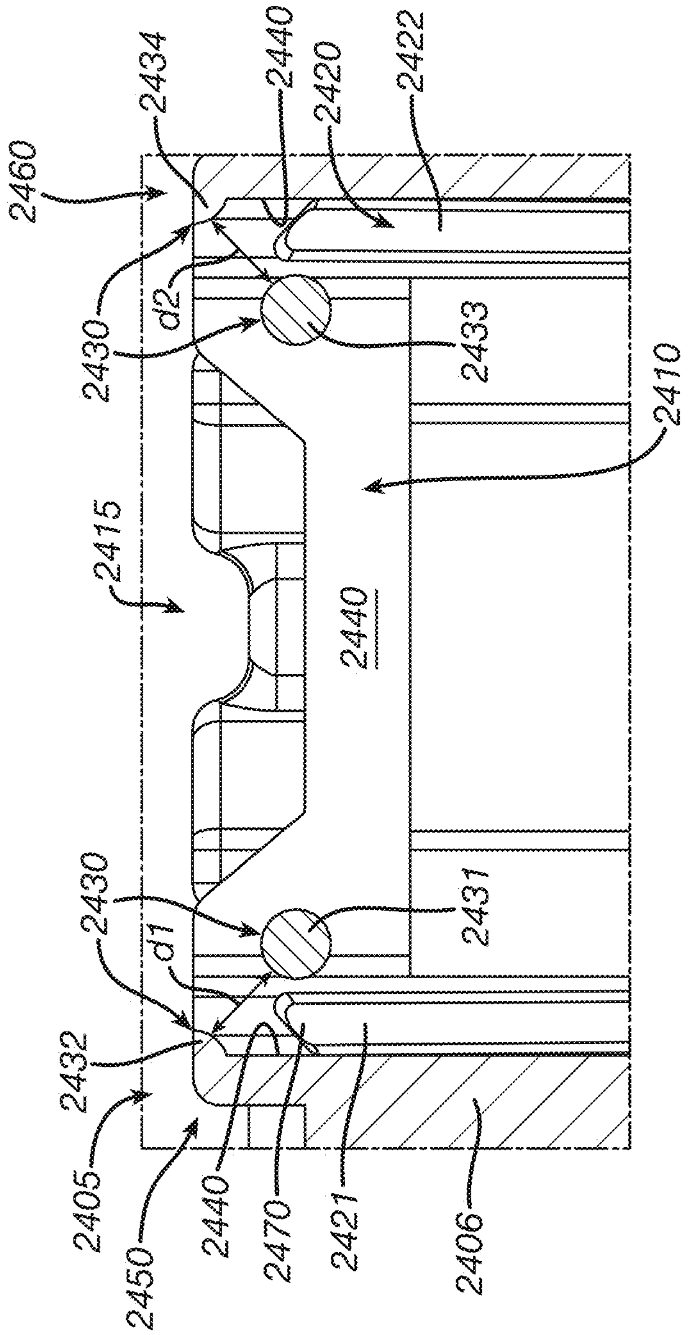
FIG. 9 depicts a cross sectional side view of a staple cartridge with staple forming features according to one embodiment.
Figure 10:
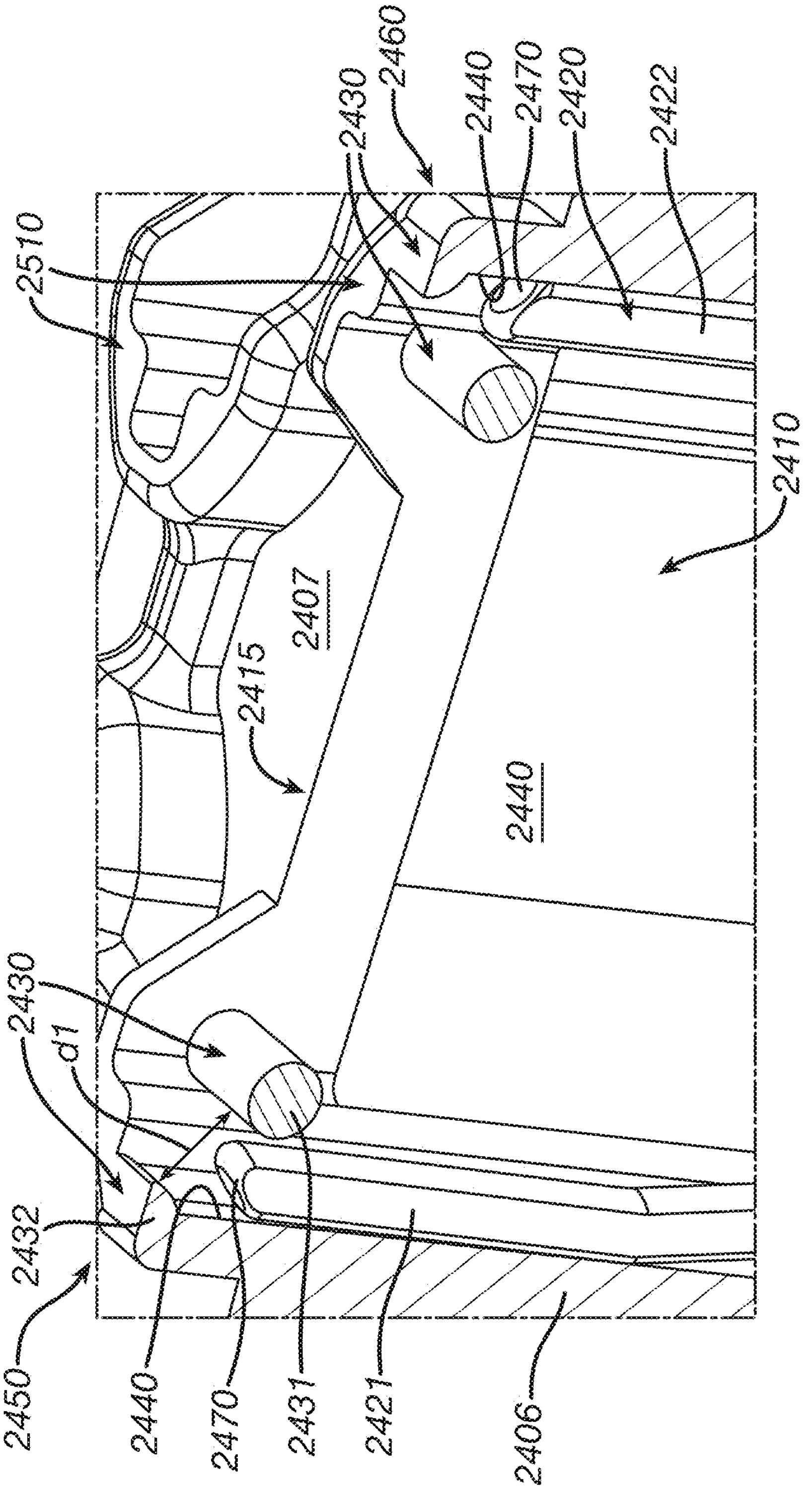
FIG. 10 depicts a cross sectional perspective view of the staple cartridge of FIG. 9 with staple forming features according to one embodiment.

FIGS. 9 and 10 depict cross sectional side and perspective views, respectively, of a staple cartridge with staple forming features according to one embodiment. The staple cartridge 2405 shown in FIGS. 9 and 10 and described below may be similar to the staple cartridge 37 described in section I above. For example, the staple cartridge 2405 of FIGS. 9 and 10 may be used with an end effector of a surgical instrument, such as end effector 12 of surgical instrument 10 described above. For instance, the end effector of the surgical instrument may be a surgical stapler having a first jaw and a second jaw, where one of the first jaw and second jaw are pivotable relative to the other, where the second jaw contains the staple cartridge 2405 described herein. The staple cartridge 2405 has a cartridge body 2406 and includes a staple pocket 2410 having an aperture or opening 2415 in a top surface or deck of the cartridge body 2406 of the staple cartridge 2405, and the staple pocket 2410 may contain an unformed staple 2420.

Similar to that described above with respect to FIG. 3, the staple cartridge 2405 may also contain a wedge sled and a plurality of staple drivers that are captured between the staple cartridge 2405 and a tray, with the wedge sled being located proximal to the staple drivers. The wedge sled is movable longitudinally within staple cartridge 2405; while staple drivers are movable vertically within staple cartridge 2405. The unformed staples 2420 are positioned within the staple pocket 2410 above corresponding staple drivers. Each unformed staple 2420 is driven vertically within the staple pocket 2410 by a staple driver to drive the unformed staples 2420 out through an associated opening 2415. In one example, the wedge sled presents inclined cam surfaces that urge staple drivers upwardly as the wedge sled is driven distally through the staple cartridge 2405.

As shown in FIGS. 9 and 10, the staple cartridge 2405 also includes two or more guide surfaces 2430 disposed adjacent the opening 2415 within the staple pocket 2410. As will be described in more detail below, some guide surfaces 2430 may be disposed directly adjacent the opening 2415

(i.e., right at the opening 2415) while other guide surfaces 2430 may be close to the opening 2415, but a short distance away from the opening 2415. In other embodiments, the guide surfaces 2430 may be positioned further away from the opening 2415 within the staple pocket 2410. The guide surfaces 2430 are configured to deform (e.g., plastically deform, bend or curl) the unformed staple 2420 as the unformed staple 2420 exits the staple pocket 2410 at the opening 2415. More specifically, the guide surfaces 2430 are configured to deform a staple leg 2421 of the unformed staple 2420 as the staple leg 2421 exits the staple pocket 2410 at the opening 2415.

In one example, the guide surfaces 2430 (also referred to herein as bending surfaces, guide features, staple forming features, or arbors) may be integrally formed with the staple cartridge 2405 (i.e., the cartridge body 2406 of the staple cartridge 2405). Specifically, the guide surfaces 2430 may be integrally formed with a sidewall 2440 of the staple pocket 2410 of the staple cartridge 2405. For instance, the staple pocket 2410 may be rectangular in shape and defined by four sidewalls 2440, including two opposing lengthwise sidewalls 2440 and two opposing shorter widthwise sidewalls 2440. In one embodiment, the guide surfaces 2430 may be a part of, and extend away from, one or both of the two opposing lengthwise sidewalls 2440. In an example, a guide surface 2430 may extend between the two opposing lengthwise sidewalls 2440. In another embodiment, the guide surfaces 2430 may be a part of, and extend outward from, one or both of the two opposing shorter widthwise sidewalls 2440. In some embodiments, such as those shown in FIGS. 9 and 10, the guide surfaces 2430 may be a part of, and extend outward from, one or both of the two opposing lengthwise sidewalls 2440 and the two opposing shorter widthwise sidewalls 2440.

In one embodiment, the guide surfaces 2430 are arbors, which, as mentioned above, are simple round or cylindrical rods, pegs, pins, deflection protrusions, and the like (or portions thereof). In some examples, the arbors 2430 may have a diameter of up to one and a half times (1.5×) the diameter of the wire of the unformed staple 2420. Other sizes are possible. The arbors 2430 may be placed at or near the exit of the staple pocket 2410, around which a staple leg wire is curled, bent, formed or shaped.

In one example, as shown in at least FIGS. 9-15, each side or end of the staple pocket 2410 includes two arbors 2430, such that there are four arbors 2430 total in the staple pocket 2410.

Referring to FIGS. 9 and 10, the staple cartridge 2405 includes a first top arbor 2432 disposed adjacent the opening 2415 at a first end 2450 of the staple pocket 2410 and a second top arbor 2434 disposed adjacent the opening 2415 at a second end 2460 of the staple pocket 2410. The first and second top arbors 2432, 2434 may be a type of surface protrusion that extends outward from respective sidewalls 2440 (e.g., two opposing shorter widthwise sidewalls 2440) where the sidewalls 2440 intersect the top surface of the staple pocket 2410 at the opening 2415. In the example shown in FIGS. 9 and 10, the first and second top arbors 2432, 2434 are quarter sections of a cylindrical pin or peg, similar to quarter round molding, at the uppermost portion of the sidewalls 2440 (i.e., the top surface of the opening 2415 at the sidewalls 2440). The first and second top arbors 2432, 2434 may span the entire width of the two opposing shorter widthwise sidewalls 2440, or may span only portions thereof. As described below in more detail, the first and second top arbors 2432, 2434 are designed and configured to deflect the legs of the unformed staple 2420 as the legs exit the staple pocket 2410.

The staple cartridge 2405 also includes a first bottom arbor 2431 offset a first distance d1 from the first top arbor 2432 and a second bottom arbor 2433 offset a second distance d2 from the second top arbor 2434. The first and second bottom arbors 2431, 2433 are cylindrical pins or pegs that extend outward from, or between, opposing lengthwise sidewalls 2440 of the staple pocket 2410. In one example, the first and second bottom arbors 2431, 2433 may span the entire distance or opening between the opposing lengthwise sidewalls 2440. In another example, the first and second bottom arbors 2431, 2433 may span only a portion of the distance or opening between the opposing lengthwise sidewalls 2440. In yet another example, each lengthwise sidewall 2440 of the two opposing lengthwise sidewalls 2440 may include a first and second bottom arbor 2431, 2433 that spans only a portion of the distance or opening between the opposing lengthwise sidewalls 2440. An example of this configuration is described below with reference to FIGS. 13A-13C.

The first distance d1 (between the first top arbor 2432 and the first bottom arbor 2431) and the second distance d2 (between the second top arbor 2434 and the second bottom arbor 2433) may be vectors made up of an x-axis component and a y-axis component, i.e., a horizontal and vertical component. In this way, a value of the first and second distances d1, d2 may not change even though their respective individual components may change. In other words, the first bottom arbor 2431 may change position relative to the first top arbor 2432 while still maintaining the first distance d1. Similarly, the second bottom arbor 2433 may change position relative to the second top arbor 2434 while still maintaining the second distance d2. The arbors 2430 can be positioned in the staple cartridge 2405 to effectuate proper staple formation. Positioning of the arbors 2430 relative to each other has an impact on the staple formation. In some cases, even the slightest change of position of one of the arbors 2430 may have a significant impact on the staple formation. For example, the horizontal and vertical (i.e., x and y) positions of the arbors 2430 are important in determining staple trajectory, and even a small amount of movement in arbor 2430 positions can make a significant difference in trajectory. In other words, the positioning and distances between arbors 2430 can affect the amount/level of curl or curl radius (i.e., radius of curvature of staple legs as the staple legs are driven out of the staple pocket 2410) and curl height (i.e., height of the staple legs as the staple legs are driven out of the staple pocket 2410).

Referring back to FIGS. 9 and 10, the staple pocket 2410 may contain an unformed staple 2420 having a first staple leg 2421 and a second staple leg 2422. The first and second staple legs 2421, 2422 may be disposed along or may abut the two opposing shorter widthwise sidewalls 2440. As mentioned above, the first and second top arbors 2432, 2434 are designed and configured to deflect the legs of the unformed staple 2420 as the legs exit the staple pocket 2410 during a firing of the staple cartridge 2405. Specifically, the first top arbor 2432 and the first bottom arbor 2431 are configured to deform the first staple leg 2421 as the first staple leg 2421 exits the staple pocket 2410 at the opening 2415 during the firing, and the second top arbor 2434 and the second bottom arbor 2433 are configured to deform the second staple leg 2422 as the second staple leg 2422 exits the staple pocket 2410 at the opening 2415 during the firing. Each of the first staple leg 2421 and second staple leg 2422 have an angled tip 2470. As the unformed staple 2420 exits the staple pocket 2410, the first staple leg 2421 is configured to pass between the first top arbor 2432 and the first bottom arbor 2431, such that the angled tip 2470 of the first staple leg 2421 contacts the first top arbor 2432 causing the first staple leg 2421 to curl toward and over the first bottom arbor 2431. Similarly, the second staple leg 2422 is configured to pass between the second top arbor 2434 and the second bottom arbor 2433, such that the angled tip 2470 of the second staple leg 2422 contacts the second top arbor 2434 causing the second staple leg 2422 to curl toward and over the second bottom arbor 2433.

Figure 11:
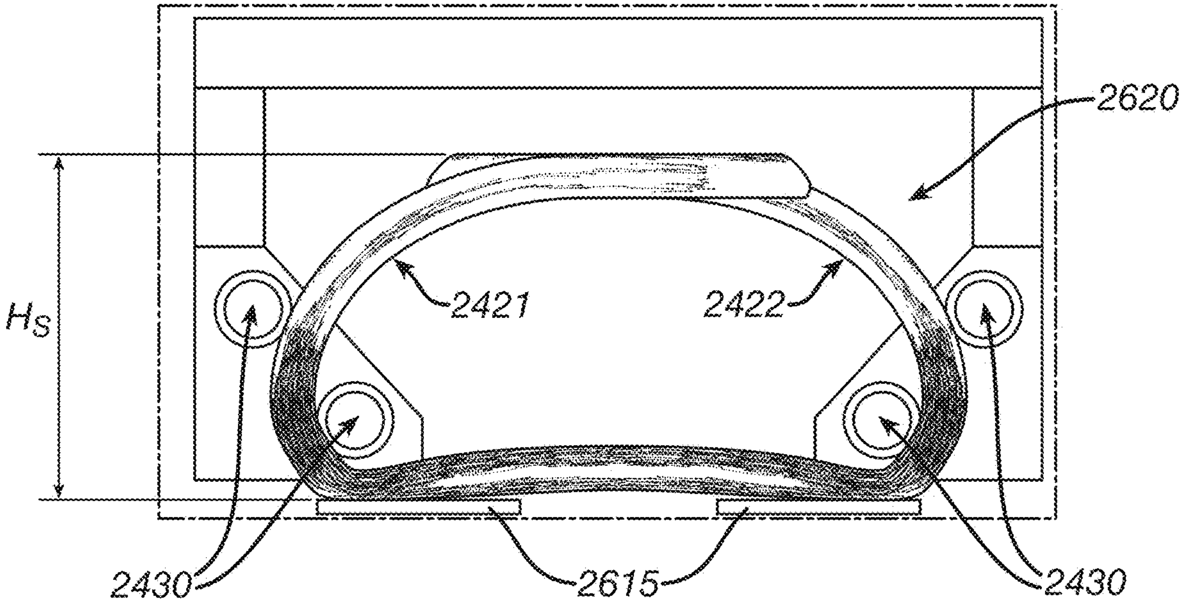
FIG. 11 depicts staple formation using arbors according to one embodiment.

FIG. 11 depicts staple formation using arbors according to one embodiment. The positioning and arrangement of the arbors 2430 of FIG. 11 is the same as that described above for FIGS. 9 and 10, i.e., two arbors (upper and lower) on each side of a staple pocket corresponding to first and second staple legs 2421, 2422, respectively. As shown in FIG. 11, during a firing of the staple cartridge 2405, a wedge sled is advanced through the staple cartridge 2405 and the wedge sled urges a staple driver 2615 upwardly, which drives the staples up and out of the staple pocket 2410. During this process, as the first and second staple legs 2421, 2422 are forced between the arbors 2430, the first staple leg 2421 and the second staple leg 2422 are deformed such that the first staple leg 2421 and the second staple leg 2422 curl toward each other to form a formed staple 2620 having a formed staple height $H_S$. The hatched portions of the staple legs 2421, 2422 in FIG. 11 indicate where the staple legs 2421, 2422 experience deformation forces.

As mentioned above, arbor locations can greatly affect the final shape of the formed staple 2620. The shape of the formed staple 2620 may depend on a tissue thickness that is being stapled (i.e., the tissue gap desired to span) and the amount of tissue to be grabbed by the formed staple 2620. The distances between the arbors 2430 is another variable to manipulate when controlling the final shape of the formed staple 2620, since distances between respective top and bottom arbors affect the degree of curvature and height of the staple curl, i.e., curl radius and curl height. For instance, in one example, when the first distance d1 and the second distance d2 are equal, a curl radius and curl height of the first staple leg 2421 is equal to a curl radius and curl height of the second staple leg 2422, respectively. This results in a substantially uniform or symmetrical formed staple 2620, such as that shown in FIG. 11. In another example, when the first distance d1 and the second distance d2 are different, a curl radius and curl height of the first staple leg 2421 is different than a curl radius and curl height of the second staple leg 2422, respectively. This results in one side of a formed staple having a tighter radius than the other side of the formed staple. In this way, the position and dimensions of arbors 2430 can be used to achieve different curl radii on different legs of the same staple, where one staple leg is deformed to have a looser radius while the other staple leg is deformed to have a tighter radius, as described in U.S. Pat. No. 12,004,744, entitled "Staple And Staple-Forming Pocket Arrangements For Surgical Staplers," filed on Sep. 27, 2021. One advantage of having differing staple curl radii of formed staples, particularly when these staples are perpendicular to a cut line, is to balance hemostasis and perfusion.

In addition to arbor 2430 positions and dimensions, staple leg geometry may also be manipulated to control the desired outcome of formed staples 2620. Specifically, changing staple leg geometries from straight to angled can change the curl on either staple leg independently. For example, staples with asymmetrical staple legs may be used, where one staple leg has a straight segment that moves through the arbors 2430 without bending while the other staple leg interfaces with the arbors 2430 the entire time it exits the staple pocket 2410. This may be desirable depending on the amount of tissue gap needed to reach across and grasp tissue. For example, with thicker tissue, if the staple legs started to curl at a tight radius immediately upon exiting the staple pocket, the height of the formed staple would not be very high, thus resulting in very little tissue being grasped by the formed staple. In another example, with thinner tissue, if the staple legs exited out of the staple pocket with a looser radius, the height of the formed staple would be larger and may be too loose to properly compress the tissue making the formed staple ineffective.

In one embodiment, staples having variable or selective leg segments may be used. For instance, a staple may have staple legs with a first or angled segment in which the staple leg extends outward/upward from the crown at an angle and a second or vertical or straight segment in which the staple leg is vertical (e.g., vertical/straight between the angled portion and the tip of the staple leg). The length of the second or vertical segment may determine how far the staple leg advances through the arbors before reaching the angled segment, which may initiate the bending (staple curling). In this way, there is a relationship between the length of the vertical segment and the tissue gap desired to span, in which the longer the vertical segment, the larger the tissue gap to span can be in order to capture thicker tissue. The angled segment may determine how much bend or curl is put into the staple leg as it lifts into the arbors. The bend or curl radius and arbor position can determine the final curl radius. A more aggressive (i.e., higher) angle of the angled segment may increase the force needed to bend or curl the staple leg, resulting in a tighter formed curl radius and therefore a tighter formed staple. In this way, the staple leg angle relative to the arbors can change the curl radius, especially as the crown of the staple approaches the arbors. Manipulating the staples and arbors in this way makes it possible to form a staple tighter than the gap between opposing jaws of a surgical stapler (i.e., the height of the formed staple is less than a distance between opposing jaws of the surgical stapler).

Another example of a staple having variable or selective leg segments includes a staple having three segments: a first vertical segment extending upward from the crown of the staple; an angled segment extending upward and outward from the first vertical segment; and a second vertical segment extending upward from the angled segment to the tip of the staple. In this example, changing the lengths of the vertical segments and the angle of the angled segment changes the final shape of the formed staple, and manipulating these variables will be based on the desired tissue gap the formed staple needs to reach across in order to grasp an appropriate amount of tissue.

In some cases, it may be desirable and advantageous to have formed staples with the same or uniform height. In other cases, it may be desirable and advantageous to have formed staples with differing heights. One way to achieve formed staples with differing heights using conventional anvils is to simply vary the distance that staple drivers are driven upward in the staple cartridge. In this case, the further the drivers are driven upwards toward the anvil, the more formed the staples become, thus having a smaller height, whereas the less the drivers are driven, the staples are less formed and have a larger height. However, in the present disclosure staples may be formed without the staples contacting an anvil jaw. Therefore, other means of achieving different formed staple heights are needed. In addition to manipulating the variables discussed above, loading a staple cartridge with unformed staples of varying heights may also help achieve the desired outcome of formed staples with varying heights. By changing the positions and dimensions of arbors and by varying unformed staple heights in the staple cartridge, formed staples with varying heights may be achieved even in situations where the tissue thickness between opposing jaws of the stapler is the same across the length of the staple cartridge and in situations in which all of the staple drivers advance upward in the staple cartridge the same amount.

As noted above, the staple cartridge 2405 of FIGS. 9 and 10 may be used with an end effector of a surgical instrument, such as a surgical stapler. In one embodiment, the surgical stapler includes a first jaw and a second jaw pivotable relative to the first jaw, the second jaw containing a staple cartridge, such as the staple cartridge 2405 described above. In this example, the staple cartridge 2405 includes a proximal end, a distal end, and a tissue supporting deck 2407. The staple cartridge 2405 also includes a plurality of rows of staple cavities 2410 defined in the deck 2407 and configured to hold unformed staples 2420. The staple cartridge 2405 further includes a staple forming feature 2430 disposed in the staple cavities 2410, a plurality of drivers 2615 configured to drive the unformed staples 2420 out of the staple cavities 2410 toward the first jaw, and a sled movable from the proximal end to the distal end of the staple cartridge 2405 during a firing stroke to lift the plurality of drivers 2615 toward the first jaw. The staple forming feature 2430 is configured to deform the unformed staples 2420 during the firing stroke to formed staples 2620 having a formed staple height $H_S$. See FIG. 11.

The staple forming feature 2430 disposed in the staple cavities 2410 may be the same as the guide surfaces and arbors discussed above. During the firing stroke, the unformed staples 2420 are deformed into the formed staples 2620 by the staple forming feature 2430 while avoiding contact with the first jaw.

In one example, the unformed staples 2420 in the plurality of rows of staple cavities 2410 have the same height. In another example, the unformed staples 2420 in at least one row of staple cavities 2410 of the plurality of rows of staple cavities 2410 have different heights.

As discussed above, formed staple heights may be uniform or varying. In one example, the formed staple height $H_S$ of the formed staples 2620 is less than a distance between the plurality of staple drivers 2615 and the first jaw at an end of the firing stroke. In another example, during the firing stroke, when a tissue thickness and a distance between the first jaw and the second jaw in which the unformed staples 2420 are formed is uniform across the plurality of rows of staple cavities 2410, and when the plurality of drivers 2615 are lifted no further than the deck 2407 of the staple cartridge 2405, the unformed staples 2420 in different rows of the plurality of rows of staple cavities 2410 are formed to different formed staple heights $H_S$. This provides the advantage of being able to control staple height formation by changing dimensions and positioning of the staple forming features 2430 and/or by providing varying heights of unformed staples 2420 in the staple cartridge 2405, as described above.

In one embodiment, a width of the formed staples 2620 is the same as a width of the unformed staples 2420.

Figure 12:
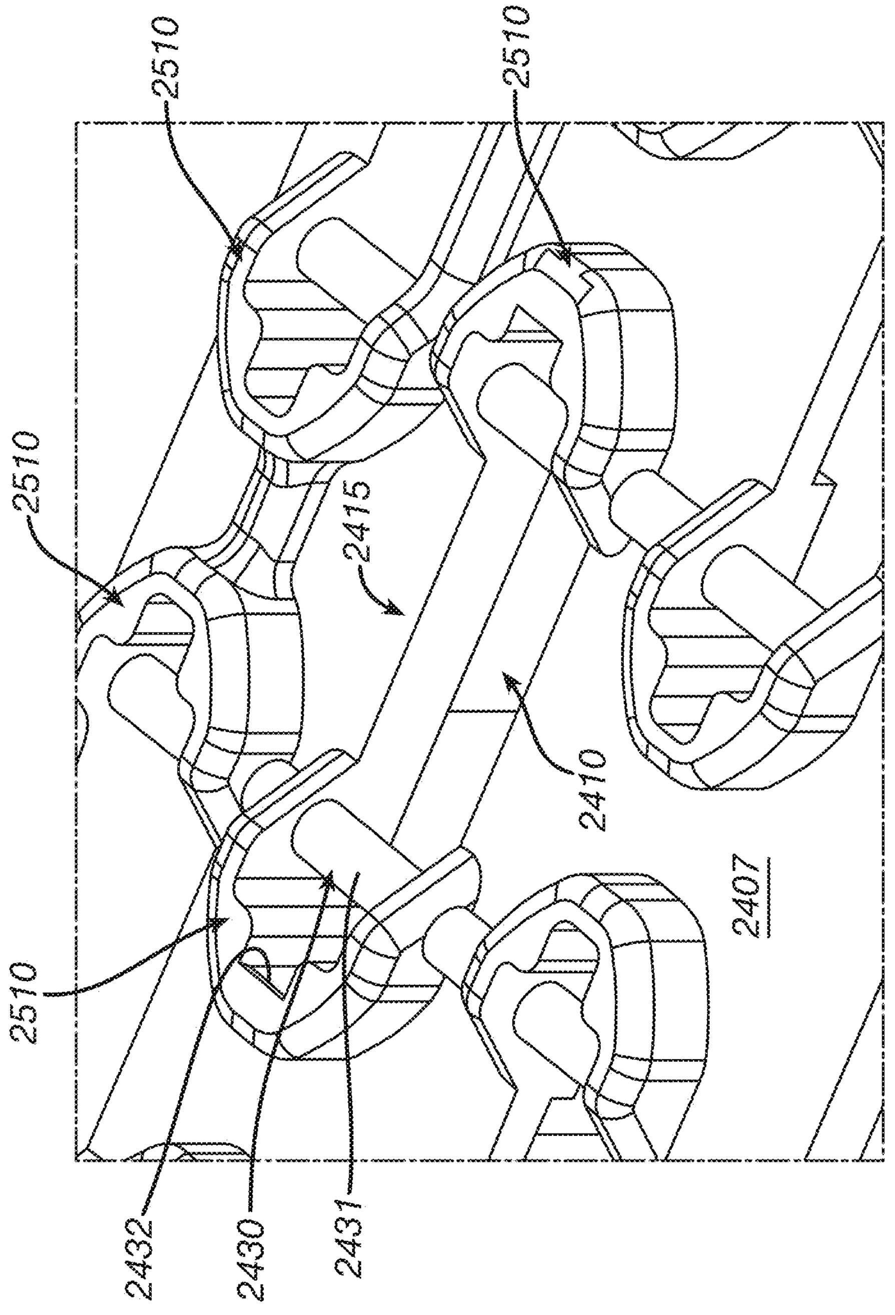
FIG. 12 depicts a perspective top view of the staple cartridge of FIGS. 9 and 10 according to one embodiment.

Referring back to the figures, FIG. 12 is perspective top view of the staple cartridge of FIGS. 9 and 10 according to one embodiment. In the example shown in FIG. 12, the guide surface 2430 includes a first arbor 2431 that spans across the opening 2415. In this case, the first arbor 2431 is a continuous arbor that spans multiple openings 2415. As shown in FIG. 12, the first arbor 2431 spans three openings 2415 of three staple pockets 2410. The staple cartridge 2405 of FIG. 12 also includes a second arbor 2432 disposed adjacent the opening 2415. The second arbor 2432 of FIG. 12 is the same as the first top arbor 2432 of FIGS. 9 and 10. As shown more clearly in FIG. 12 than in the cross sectional views of FIGS. 9 and 10, the span of the second arbor 2432 is shorter than the span of the first arbor 2431. In one example, the span of the second arbor 2432 corresponds to a size of a staple leg.

Similar to above, the first arbor 2431 and the second arbor 2432 are offset from one another vertically and horizontally within the staple pocket 2410. The second arbor 2432 is disposed at an end of the staple pocket 2410, while the first arbor is offset closer towards the center of the staple pocket 2410.

In the example shown in FIGS. 9, 10, and 12, the staple cartridge 2405 includes a tissue gripping feature 2510 disposed at the opening 2415 of the staple pocket 2410. The tissue gripping feature 2510, or gripping surface technologies, may be features disposed on the cartridge deck 2407 designed and configured to grip against tissue when tissue is grasped between opposing jaws of the surgical stapler. These features interact (i.e., contact, engage, etc.) with the tissue held against the cartridge deck 2407 to help prevent tissue movement during a firing stroke of the surgical stapler. As shown in FIGS. 9, 10, and 12, the guide surface 2430 (e.g., either the first or second arbor 2431, 2432) is disposed within the tissue gripping feature 2510. In this case, the first and second arbors 2431, 2432 are both located above a central portion of the opening 2415 of the staple pocket 2410, since the first and second arbors 2431, 2432 are both disposed in the tissue gripping feature 2510, which is disposed on the cartridge deck 2407. However, in another embodiment without a tissue gripping feature 2510, where the entire opening 2415 is on the same level as the cartridge deck 2407, the first and second arbors 2431, 2432 would both be located below the opening 2415 of the staple pocket 2410.

In either arrangement, the relative position and orientation of the arbors 2430 with respect to each other remain the same and thus provide the same staple curling functions as described above. Specifically, the staple leg 2421 is configured to exit the staple pocket 2410 between the first arbor 2431 and the second arbor 2432, such that the first arbor 2431 and the second arbor 2432 deform the staple leg 2421 as the staple leg 2421 exits the staple pocket 2410. This allows staple formation while avoiding contact with a distant anvil.

The staple forming features and functionality described herein must still allow the staples to release from the staple cartridge 2405. In one example, the arbors 2430 may be pushed out of their supports (such as the tissue gripping features 2510) by a driver at the top of the firing stroke and released with staples. Other examples include frangible arbors, deployable arbor sets, retractable arbor sets, or arbors having a slidable engagement with a driver to move and release the staple.

In one embodiment, a frangible or plastically deformable static arbor may be used to form the staple curl (e.g., to bend the staple during the firing stroke), but then allow the crown of the staple to pass the arbor when the driver completes the firing stroke. In this case, an interrupted, broken, or segmented arbor may be used to release the staple. The arbor positions and orientations relative to one another can remain the same as discussed above, except that one of the arbors (e.g., the longer arbor 2431 spanning the opening that lies in the path of the crown) has an opening or break in the center (e.g., halfway across the opening) to allow the crown to pass through the arbor 2431. The edges of the portions of the arbor 2431 defining the opening may be radiused edges to allow smooth movement of the staple along the surfaces of the arbors during curling. The wire of the staple will interface with the arbor, and cause curling, as discussed above. The features (e.g., arbors) may be integral with the cartridge, also as discussed above. The arbors being integral with the cartridge may allow to use molds, especially if the arbors are designed to be on an edge of feature that is already being molded. This would simply the manufacturing of the cartridges to contain arbors. An interrupted arbor has the advantage in that as the driver is raised within the staple cartridge to finish the staple firing, the staple crown can "pop" past or through the interruption or break in the arbor, meaning that with enough force, the crown is squeezed past or through the break or interruption. In some cases, the interrupted arbor may even deform (either plastically or elastically) enough to allow the staple crown to pass through, thereby releasing the staple.

Figure 13A:
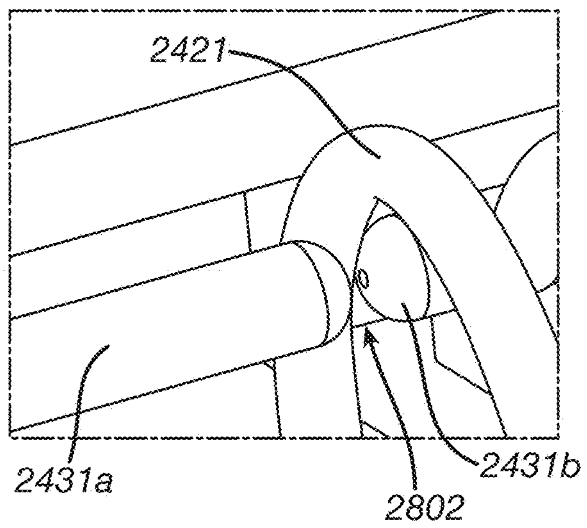
FIGS. 13A-13C depict an interrupted arbor according to one embodiment.
Figure 13B:
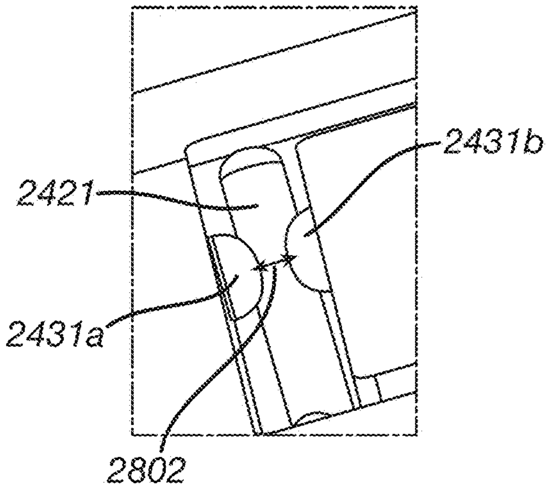
Figure 13C:
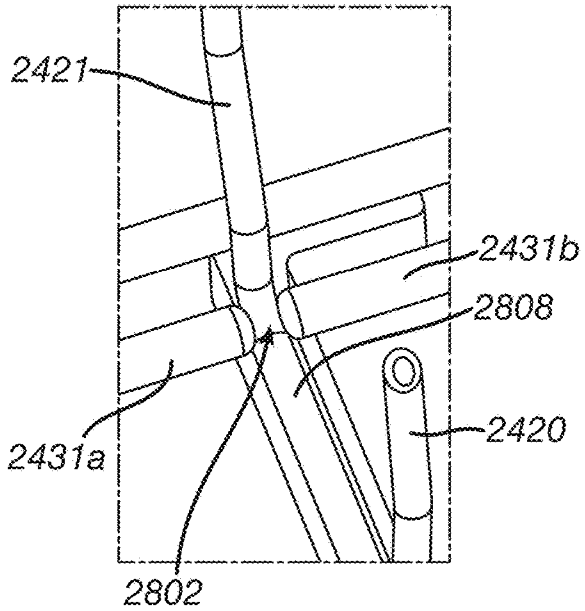

FIGS. 13A-13C depict an interrupted arbor according to one embodiment. As shown in FIGS. 13A-13C, the first arbor 2431 described above includes an interrupted arbor having a first portion 2431*a* and a second portion 2431*b* spaced apart from, and axially aligned with, the first portion 2431*a*. The first portion 2431*a* and second portion 2431*b* of the interrupted arbor are spaced apart by a gap 2802, or opening in the center to allow the crown 2808 of the staple (at this point in the formed state) to pass through (i.e., between the first portion 2431*a* and second portion 2431*b* of the interrupted arbor).

As shown in FIGS. 13A and 13B, the ends and edges of the first portion 2431*a* and second portion 2431*b* of the interrupted arbor are radiused or rounded. This still allows the staple leg 2421 to be curled against the radiused surfaces of the first portion 2431*a* and second portion 2431*b* of the interrupted arbor.

In one example, as shown in FIGS. 13B and 13C, a distance of the gap 2802 is less than a diameter of a crown 2808 of the unformed staple 2420.

As shown in FIG. 13C, when the driver reaches the top of the firing stroke, the crown 2808 of the staple is able to pass through (i.e., between) the first portion 2431*a* and second portion 2431*b* of the interrupted arbor. The force of the driver in the upward direction causes the crown 2808 to either squeeze through the gap 2802 or deform (plastically or elastically) the first portion 2431*a* and second portion 2431*b* of the interrupted arbor to deflect enough to allow the crown 2808 to pass through.

Figure 14A:
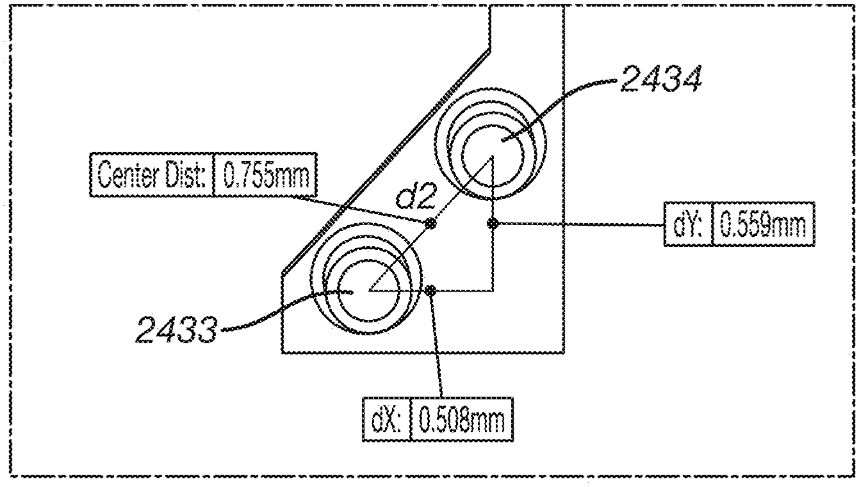
FIGS. 14A and 14B depict an arrangement of arbors according to one embodiment.
Figure 14B:
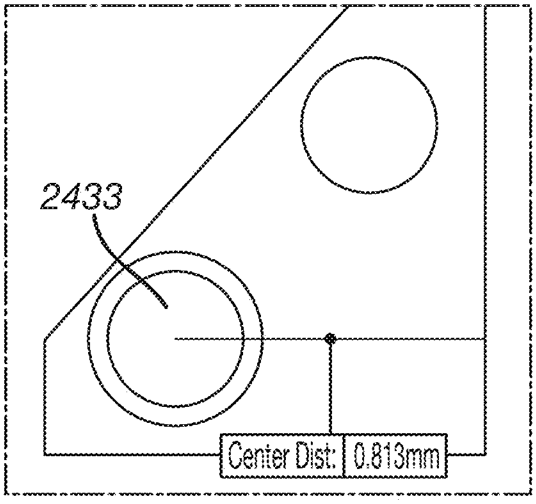

FIGS. 14A and 14B depict an arrangement of arbors according to one embodiment. As shown in FIG. 14A, the position of two arbors relative to each other, such as the second bottom arbor 2433 relative to the second top arbor 2434, is shown in more detail. Specifically, the x and y (horizontal and vertical) distances between the center of the arbors 2433, 2434 are shown. Also, the vector offset distance d2 is also shown. As shown in FIG. 14B, the position of a bottom arbor, such as the second bottom arbor 2433, relative to the sidewall of the staple pocket, such as one of the two opposing shorter widthwise sidewalls 2440 of staple pocket 2410, is shown in more detail. While FIGS. 14A and 14B illustrate specific measurements for one embodiment, other values of the dimensions shown may be used. For instance, the vector offset distance d2 between the center of the second bottom arbor 2433 and the center of the second top arbor 2434 may range between about 0.020 and 0.035 inch, in one example, and more specifically may be 0.030 inch in another example. Similarly, the x and y (horizontal and vertical) distances between the center of the arbors 2433, 2434 may range between about 0.015 and 0.025 inch, in one example, and more specifically between about 0.020 and 0.022 inch in another example. The distance between the center of the second bottom arbor 2433 and the sidewall 2440 of the staple pocket 2410, as shown in inset (b), may range between about 0.015 and 0.020 inch, in one example, and more specifically about 0.019 inch in another example. The vertical distance between the center of the second bottom arbor 2433 and the top of the tissue gripping feature 2510 of the staple cartridge deck 2407 may be between 0 to 0.025 inch in one example, and more specifically about 0.014 to 0.022 inch in another example. The distances described above are representative when using a staple wire of about 0.009 inch diameter, and round arbors that are about 0.014 inch diameter. Because the relative positions of the arbors and the wire size cause the interference that bends the staple, these distances may be scaled proportional to different staple wire diameters to achieve similar effects for slightly smaller or larger staple wires, for example.

Figure 15:
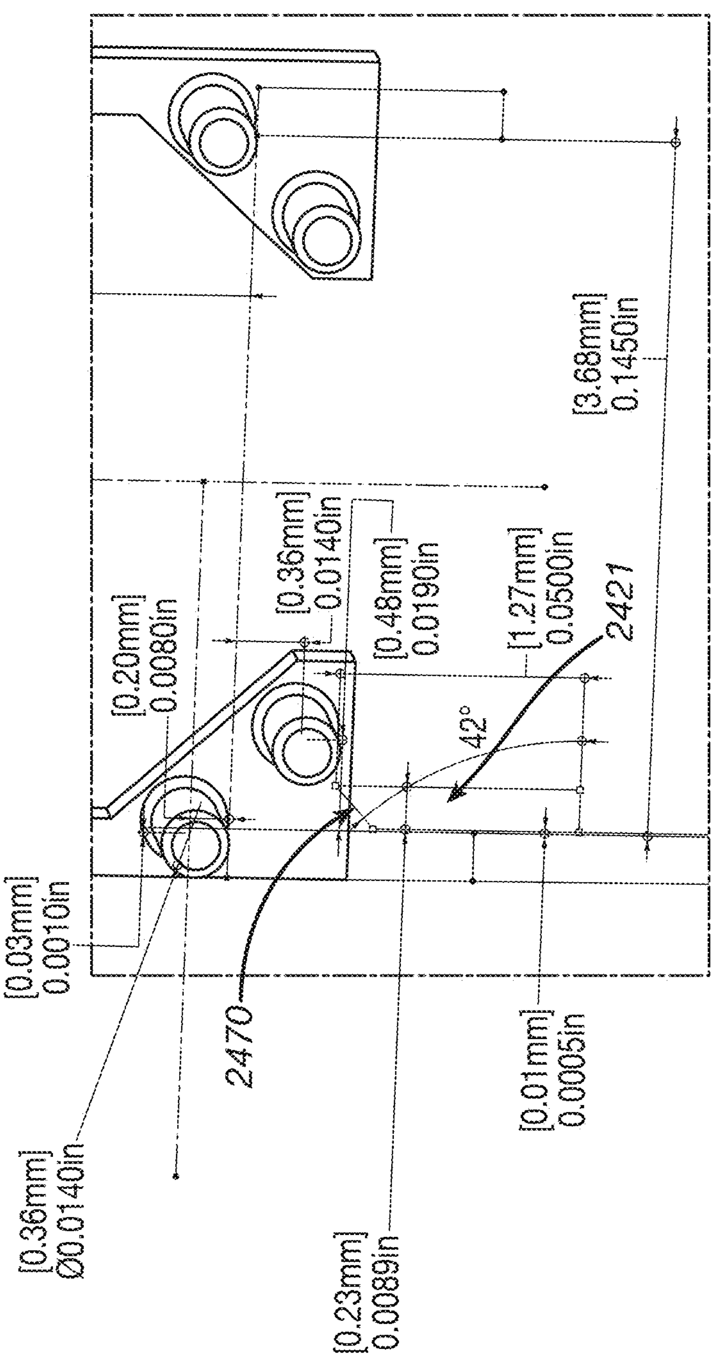
FIG. 15 depicts an arrangement of arbors according to one embodiment.

FIG. 15 depicts an arrangement of arbors according to one embodiment, where the arbors have a diameter of approximately 0.014 inch. FIG. 15 illustrates specific values for other measurements of an arbor arrangement, in one example. Included in FIG. 15 is the relative and/or specific positioning and dimensions of the first staple leg 2421 having the angled tip 2470 positioned below the arbors prior to firing.

III. Multi-Part Staple with Separate Legs and Crown to Facilitate Staple Release from Arbors As discussed above, staple forming surfaces or features, such as arbors, may be fixed (i.e., static) and disposed on an inner wall or surface of a staple cartridge pocket or opening. The arbors may be positioned at or near the exit of the cartridge pocket (also referred to as a staple pocket) such that the staple legs of a staple are curled by the arbors as the staple legs exit the staple pocket. There are advantages of having static staple forming features, or arbors. For instance, having arbors being integral with the cartridge may allow to use molds, especially if the arbors are designed to be on an edge of feature that is already being molded. This would simply the manufacturing of the cartridges to contain arbors.

However, with static arbors there is problem of advancing the staple crown past the arbors in order to exit the staple cavity. As described above, in order to contact and deform (e.g., curl) staple legs, arbors are disposed in or near the staple cavity within the path of the staple being driven out of the staple cavity. If a single, continuous arbor spanned the staple pathway, the pathway would be blocked, and the crown of the staple would not be able to advance past the arbor to exit the staple cavity. In this case, the staple would remain in the staple cartridge and be ineffective. In many cases, as shown and described above, while a width of the staple crown may be narrower than the uppermost or outer arbors, the lower or inner arbors are the ones that interfere with the crown bypassing those arbors.

A staple cartridge having the staple and arbor arrangement described below solves this problem by using arbors and a multi-part, or deconstructed, staple with separate legs and crown pieces to facilitate staple release from the arbors. In this embodiment, the staple crown is located above the lower arbors so that as the staple legs curl, the lower or inner arbors do not get trapped inside the staple. In another embodiment, the crown piece includes staple forming features, such as apertures in the form of curved passageways, that initiate staple curling as the staple legs pass through the apertures of the crown piece. In this case, additional arbors may or may not be necessary.

Figure 16:
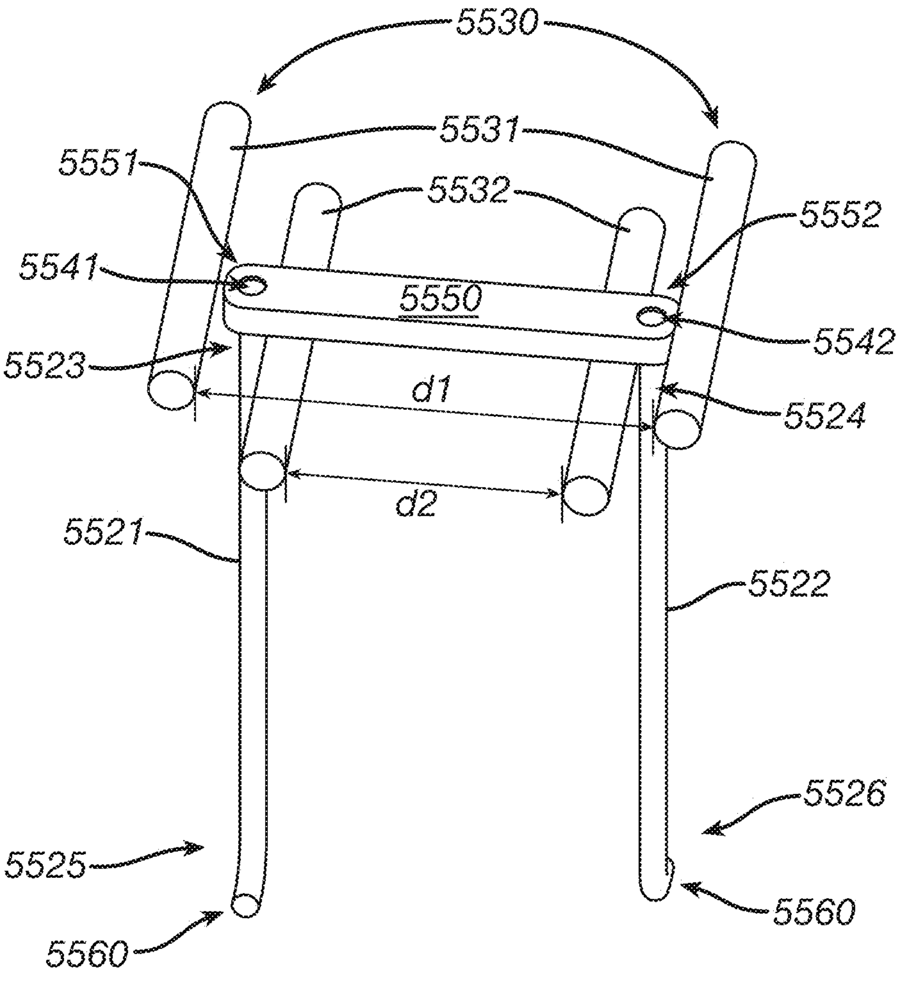
FIG. 16 depicts a perspective view of a set of arbors and a multi-part staple according to one embodiment.

FIG. 16 depicts a perspective view of a set of arbors and a multi-part staple according to one embodiment. As shown in FIG. 16, the multi-part staple (also referred to herein as a deconstructed staple) has several components that get assembled during a firing stroke to form a final formed staple using arbors on or in the staple cartridge. The staple cartridge includes a set of arbors 5530 disposed adjacent a staple pocket having an opening, the set of arbors 5530 including an upper set of arbors 5531 and a lower set of arbors 5532 disposed vertically below the upper set of arbors 5531. The set of arbors 5530 may be static arbors and may be the same type of arbors as described above. The staple cartridge also includes a multi-part staple including a first leg or first staple leg portion 5521, a second leg or second staple leg portion 5522, and a crown portion 5550 (also referred to herein as a pledget). In one example, the first and second staple leg portions 5521, 5522 may each be a single, cylindrical staple wire. The crown portion 5550 is disposed vertically between the upper set of arbors 5531 and the lower set of arbors 5532. In other words, the crown portion 5550 sits on top of, or is supported by, the lower set of arbors 5532.

The crown portion 5550 includes a first aperture 5541 disposed at a first end 5551 of the crown portion 5550 and a second aperture 5542 disposed at a second end 5552 of the crown portion 5550. The first aperture 5541 is configured to receive the first staple leg portion 5521 and the second aperture 5542 is configured to receive the second staple leg portion 5522.

Figure 17B:
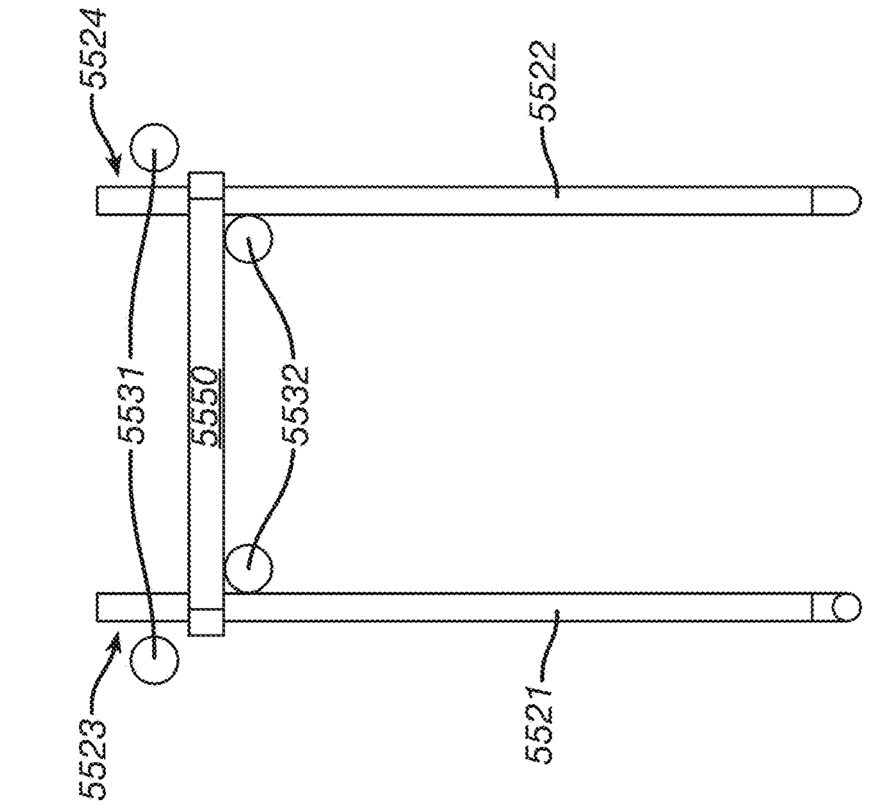
FIGS. 17A and 17B depict a side view of the set of arbors and the multi-part staple of FIG. 16 according to one embodiment.
Figure 17A:
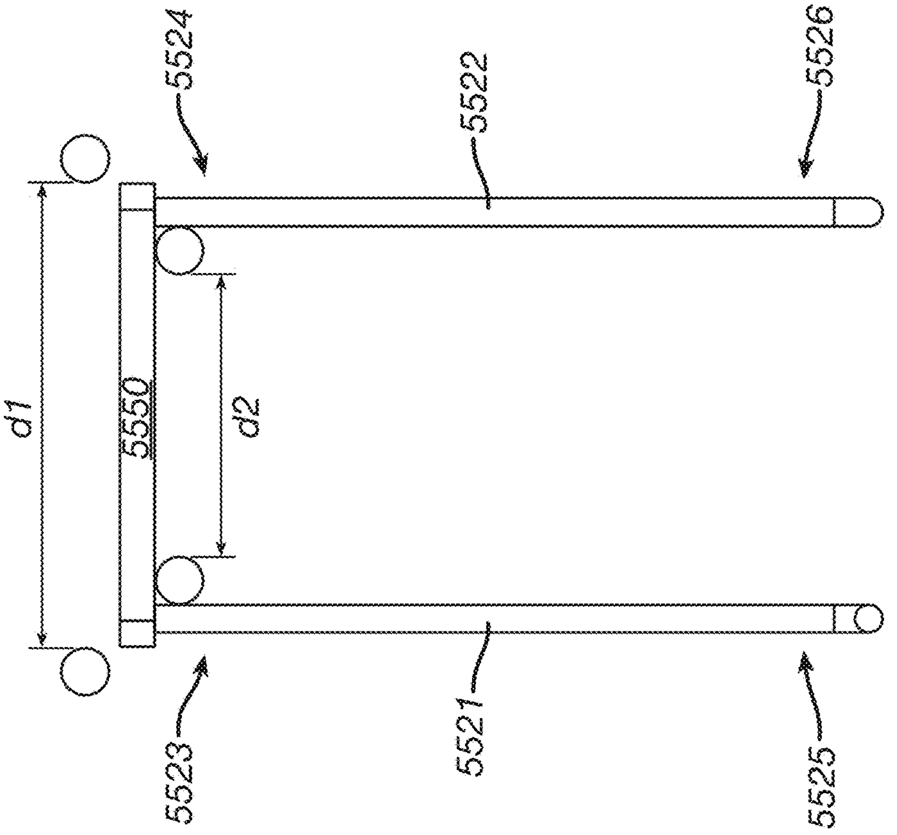

FIGS. 17A and 17B depict a side view of the set of arbors and the multi-part staple of FIG. 16 according to one embodiment. In one example, the set of arbors 5530 may be pre-formed into the staple pocket. To load the staples, the crown portion 5550 may be placed on top of the lower set of arbors 5532 and then the first staple leg portion 5521 and the second staple leg portion 5522 may be guided through the bottom of the staple pocket and into the first and second apertures 5541, 5542. Such arrangements allow the staple pockets to have two discrete paths, one for each leg. In other words, rather than a typical staple pocket that holds a traditional unformed staple, the multi-part stable described herein would only need two holes in the bottom of the staple cartridge to be received therein. In this example, the staple legs 5521, 5522 can be inserted into respective openings in the staple cartridge, where the respective openings can be configured to guide the staple legs 5521, 5522 into the apertures 5541, 5542 of the crown portion 5550.

As shown in FIG. 17A, a first end 5523 of the first staple leg portion 5521 and a first end 5524 of the second staple leg portion 5522 is configured to pass through the first aperture 5541 and the second aperture 5542 of the crown portion 5550, respectively, during the firing stroke. During the firing stroke, the first staple leg portion 5521 and the second staple leg portion 5522 are driven upwards between the lower set of arbors 5532, through the first and second apertures 5541, 5542, respectively, and then between the upper set of arbors 5531. This is shown in FIG. 17B. FIGS. 17A and 17B are drawn for illustration purposes, and the positions of the arbors, for example, are not to scale.

As shown in FIGS. 16 and 17, in one embodiment, arbors of the upper set of arbors 5531 are spaced apart by a first distance d1 and arbors of the lower set of arbors 5532 are spaced apart by a second distance d2 less than the first distance d1.

Figure 18:
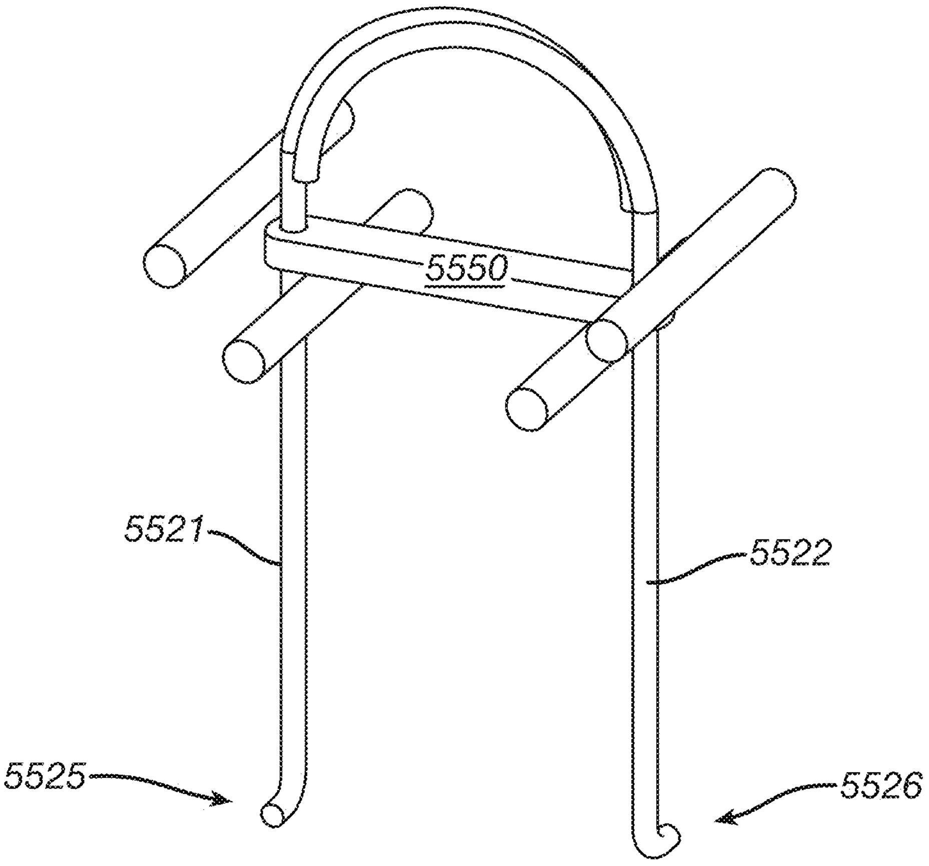
FIG. 18 depicts a perspective view of a set of arbors curling a multi-part staple according to one embodiment.

FIG. 18 depicts a perspective view of a set of arbors curling a multi-part staple according to one embodiment. As shown in FIG. 18, the set of arbors 5530 are configured to curl the first staple leg portion 5521 and the second staple leg portion 5522 as the first staple leg portion 5521 and the second staple leg portion 5522 exit the staple pocket at the opening during a firing stroke. In some cases, only one set of the set of arbors 5530 is configured to curl the staple legs 5521, 5522, such as the upper set of arbors 5531. In this case, as described in more detail below, the first and second apertures 5541, 5542 themselves may act as lower arbors, where each aperture 5541, 5542 includes surfaces able to react to load and help bend the first staple leg portion 5521 and the second staple leg portion 5522. In other words, each aperture 5541, 5542 may have a surface such that as the staple leg portions 5521, 5522 exit the apertures 5541, 5542 and contact the upper set of arbors 5531, the staple leg portions 5521, 5522 bend away from the upper set of arbors 5531 and the curl over the surfaces of the apertures 5541, 5542.

Referring back to FIG. 16, in various embodiments, a second end 5525 of the first staple leg portion 5521 includes a feature 5560 to prevent the second end 5525 (or a portion thereof) of the first staple leg portion 5521 from passing through the first aperture 5541 of the crown portion 5550 during the firing stroke. Similarly, a second end 5526 of the second staple leg portion 5522 includes a feature 5560 to prevent the second end 5526 (or a portion thereof) of the second staple leg portion 5522 from passing through the second aperture 5542 of the crown portion 5550 during the firing stroke. In this way, once the first staple leg portion 5521 and the second staple leg portion 5522 are almost completely driven out of the staple pocket, the features 5560 of the second ends 5525, 5526 of the first and second staple legs 5521, 5522 contact or engage the crown portion 5550, more specifically the bottom surface of the crown portion 5550, to facilitate interlocking between the staple legs 5521, 5522 and to ensure the crown portion 5550 is driven out of the staple pocket with the staple legs 5521, 5522. In this regard, the crown portion 5550 releases with the first staple leg portion 5521 and the second staple leg portion 5522 into tissue upon completion of the firing stroke. In other words, the crown portion 5550 or pledget 5550 is configured to release with the first leg 5521 and the second leg 5522 upon completion of the firing stroke. In this way, the lower set of arbors 5532 do not get trapped inside the formed staple.

Figure 19A:
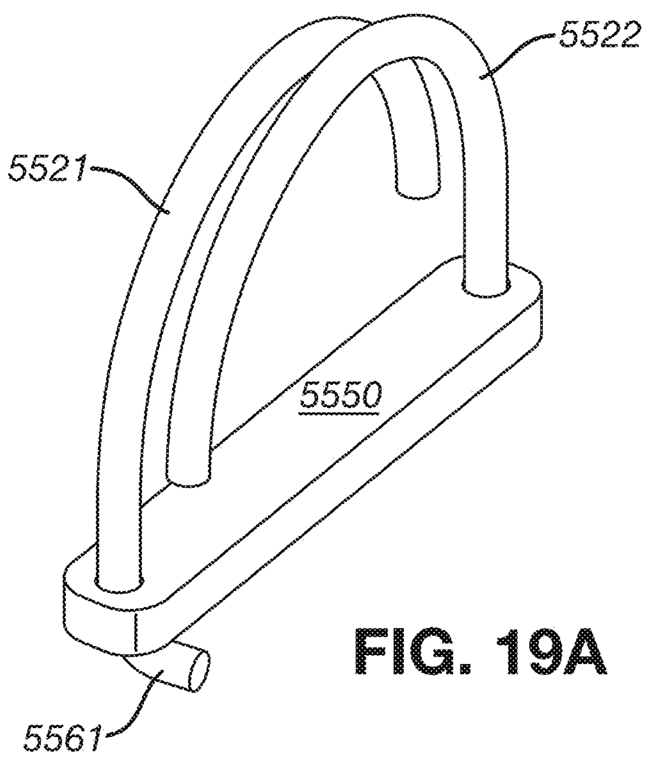
FIGS. 19A and 19B depict a front view and perspective view of a formed multi-part staple according to one embodiment.
Figure 19B:
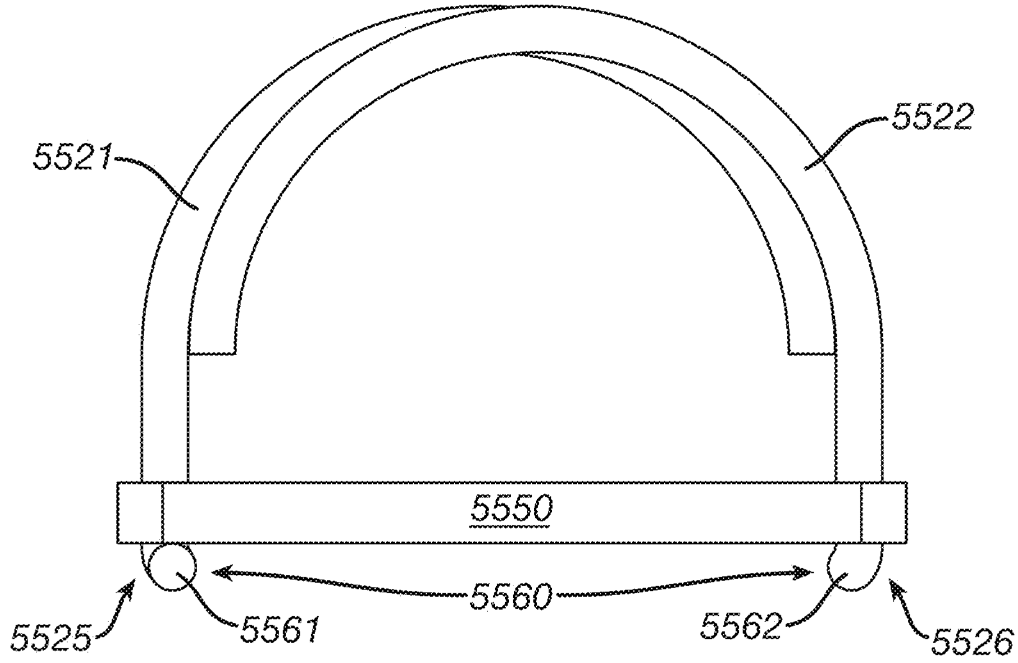
Figure 20:
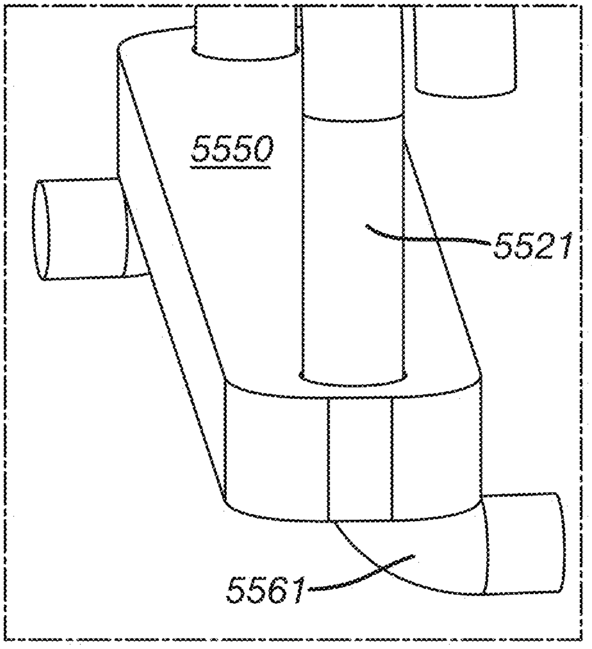
FIG. 20 depicts an enlarged perspective view of a multi-part staple according to one embodiment.

FIGS. 19A and 19B depict a perspective view and front view of a formed multi-part staple, respectively, according to one embodiment. In one embodiment, the feature 5560 includes an out of plane bend of the second end 5525, 5526 of the first and second staple leg portions 5521, 5522, as shown in FIGS. 16, 18, and 20. FIG. 20 depicts an enlarged perspective view of a multi-part staple according to one embodiment. Specifically, FIG. 20 depicts an enlarged view of the feature 5560 being an out of plane bend. As shown in FIG. 20, the out of plane bend results in the staple leg forming a "J" shape that is designed and configured to catch the crown portion 5550 and lift the crown portion 5550 up and out of the staple pocket during and upon completion of the firing stroke. While the "J" shape out of plane bend is one example of the feature, other features are contemplated. For instance, in another embodiment, the feature 5560 may include an end cap having a diameter larger than a diameter of the first and second apertures 5541, 5542. In yet another embodiment, the staple legs 5521, 5522 may taper in diameter at the second ends, such that the second ends gradually increase in diameter towards the tips of the staple legs 5521, 5522. In this case, as the staple legs 5521, 5522 advance through the apertures 5541, 5542, the larger diameter ends or tips of the staple legs 5521, 5522 do not fit through the apertures 5541, 5542 and the crown portion 5550 is released with the staple legs 5521, 5522. In other words, the crown portion 5550 and the staple legs 5521, 5522 deploy as a final, formed staple, as shown in FIGS. 19A and 19B.

In one embodiment, a staple cartridge includes a set of arbors 5530 disposed adjacent a staple pocket having an opening, the set of arbors 5530 including an upper set of arbors 5531 and a lower set of arbors 5532 disposed vertically below the upper set of arbors 5531. The staple cartridge can include a multi-part staple including a first leg 5521, a second leg 5522, and a pledget 5550, where the pledget 5550 is disposed on top of the lower set of arbors 5532. In this embodiment, at least the upper set of arbors 5531 are configured to curl the first leg 5521 and the second leg 5522 as the first leg 5521 and the second leg 5522 exit the staple pocket at the opening during a firing stroke.

The pledget 5550 can include a plurality of apertures 5541, 5542 defined therein which can be configured to slidably receive and/or guide the legs 5521, 5522 of a staple therein. For example, the pledget 5550 can include a first aperture 5541 disposed at a first end 5551 of the pledget 5550 and configured to receive the first leg 5521, and a second aperture 5542 disposed at a second end 5552 of the pledget 5550 and configured to receive the second staple leg 5522. In addition to or in lieu of the apertures 5541, 5542, a pledget 5550 can include any suitable opening such as a slot, guide, and/or groove, for example, which can be configured to slidably receive and/or guide the staple legs 5521, 5522. In certain embodiments, as illustrated in FIGS. 17A and 17B, the tips 5523, 5524 (or top portions) of the staple legs 5521, 5522 can be positioned within the apertures 5541, 5542 when the staples are in their unfired positions. In at least one such embodiment, the tips of the staple legs 5521, 5522 can protrude above the pledget 5550 when the staples are in their unfired position. In certain other embodiments, the tips of the staple legs 5523, 5524 may be positioned just below the pledget 5550 when the staples are in their unfired positions such that, when the staples are moved upwardly through the staple pocket, the staple legs 5521, 5522 can enter into the apertures 5541, 5542 of the pledget 5550 and slide therethrough. In any event, when the legs 5521, 5522 of the staples are positioned within the pledget 5550, the lateral and/or longitudinal movement of the staple legs 5521, 5522 can be limited without preventing the upward movement of the staple legs 5521, 5522 when the staples are deployed. When the staples are deployed, the staple legs 5521, 5522 can slide upwardly through the pledget 5550 to penetrate the tissue T, curl based on contact with the set of arbors 5530, and deform downwardly to form the final staple and capture the tissue therein, as shown in FIGS. 19A and 19B.

Similar to above, in this embodiment, as shown in FIGS. 19A and 19B, the first leg 5521 includes a first end 5523 configured to pass through the first aperture 5541 and a second end 5525 opposite the first end 5523, the second end 5525 including a first feature 5561 to prevent the second end 5525 from passing through the first aperture 5541 during the firing stroke. Likewise, the second leg 5522 includes a first end 5524 configured to pass through the second aperture 5542 and a second end 5526 opposite the first end 5524, the second end 5526 including a second feature 5562 to prevent the second end 5526 from passing through the second aperture 5542 during the firing stroke. The first feature 5561 and the second feature 5562 include an out of plane bend of the second end 5525, 5526 of the first and second staple leg portions 5521, 5522. In one embodiment, the out of plane bend of the second end 5525 of the first leg 5521 is in a first direction, and the out of plane bend of the second end 5526 of the second leg 5522 is in a second direction opposite the first direction. In some examples, the first feature 5561 and the second feature 5562 include an end cap having a diameter larger than a diameter of the first and second apertures 5541, 5542.

In one example, respective first ends 5523, 5524 of respective first and second legs 5521, 5522 are configured to pass through the first and second apertures 5541, 5542, respectively, during the firing stroke, and wherein respective second ends 5525, 5526 opposite respective first ends 5523, 5524 of respective first and second legs 5521, 5522 are configured to engage a bottom surface of the pledget 5550 upon completion of the firing stroke, such that the pledget 5550 is driven out of the staple pocket with the first and second legs 5521, 5522.

In yet another embodiment, the apertures 5541, 5542 in the crown portion or pledget 5550 may act as an arbor, or staple forming feature or surface. In other words, the apertures 5541, 5542 may be deforming apertures within a crown portion of pledget 5550. For example, a staple cartridge includes a staple pocket having an opening and a multi-part staple. The multi-part staple includes a first leg 5521, a second leg 5522, and a pledget 5550. In this example, the pledget 5550 includes a first aperture 5541 disposed at a first end 5551 of the pledget 5550 and configured to receive the first leg 5521, and a second aperture 5542 disposed at a second end 5552 of the pledget 5550 and configured to receive the second staple leg 5522.

In this embodiment, the first aperture 5541 is configured to curl the first leg 5521 as the first leg 5521 passes through the first aperture 5541 during a firing stroke. Similarly, the second aperture 5542 is configured to curl the second leg 5522 as the second leg 5522 passes through the second aperture 5542 during the firing stroke. Similar to above, the pledget 5550 is configured to release with the first leg 5521 and the second leg 5522 upon completion of the firing stroke.

Figure 21A:
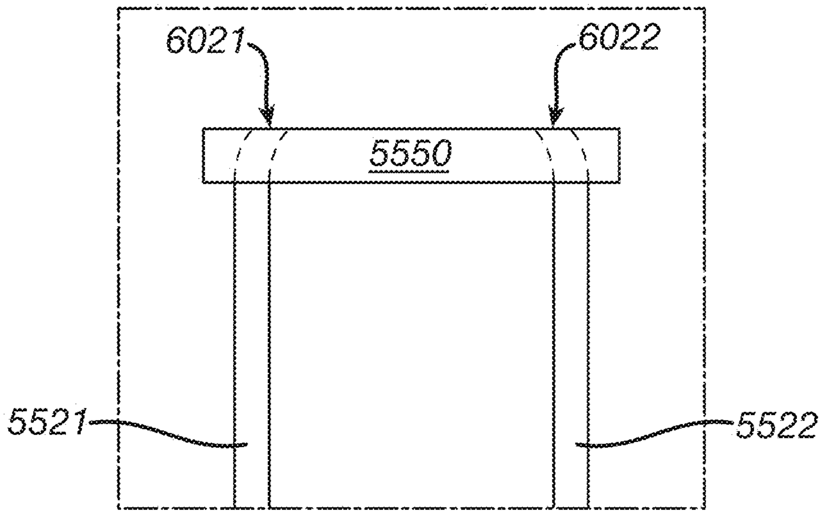
Figure 21B:
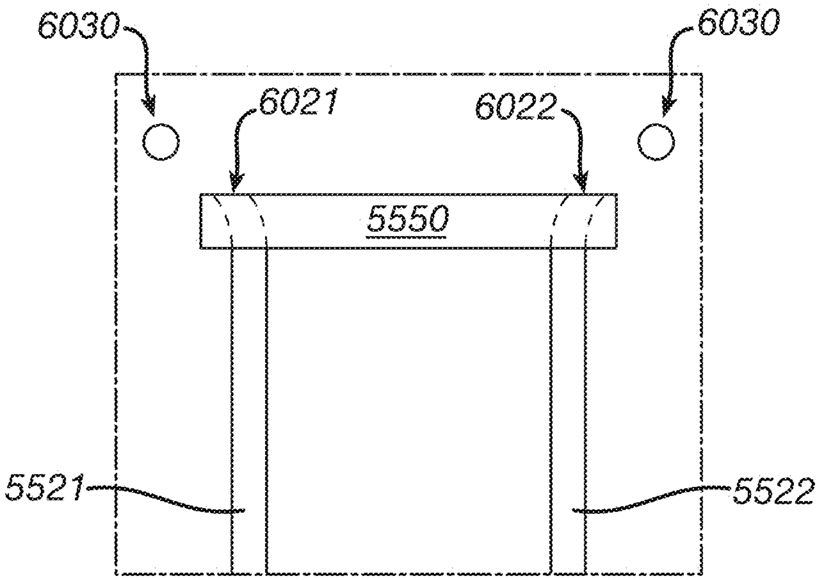

FIGS. 21A and 21B depict deforming apertures within a pledget 5550 according to one embodiment. As shown in FIGS. 21A and 21B, the first aperture 5541 comprises a first curved passageway 6021, such that the first leg 5521 plastically deforms in a first direction as the first leg 5521 passes through the first curved passageway 6021. Similarly, the second aperture 5542 comprises a second curved passageway 6022, such that the second leg 5522 plastically deforms in a second direction as the second leg 5522 passes through the second curved passageway 6022. In one example, the first direction and the second direction are opposite each other. FIGS. 21A and 21B show the curved passageways 6021, 6022 curving in different directions. Having staple forming features within a crown portion or pledget 5550 may eliminate the need for some (or all) of the arbors. However, if the lower set of arbors, such as lower set of arbors 5532, are removed, the pledget 5550 would need to be held in place by another mechanism, device, or structure, such as small pins or rods extending underneath the pledget 5550 within the staple pocket.

The passageways 6021, 6022 going through the pledget 5550 may not only curve in the x-y coordinate plane, but the passageways 6021, 6022 of the pledget 5550 may also curve or extend through the pledget 5550 in the z-coordinate direction. In other words, if the passageways 6021, 6022 extending through the pledget 5550 are angled properly, the staple legs 5521, 5522 can curl out of plane while exiting the apertures 5541, 5542 of the pledget 5550. This would result in the final staple having a 3D shape, such as shown in FIG. 19A, and as disclosed in U.S. patent application Ser. No. 18/781,566, entitled "Staple Cartridge With Static Angled Arbors To Form Three-Dimensional (3D) Staples," filed on Jul. 23, 2024, the disclosure of which is incorporated by reference herein, in its entirety.

Similar to above, the first leg 5521 includes a first end 5523 configured to pass through the first aperture 5541 and a second end 5525 opposite the first end 5523, the second end 5525 including a first feature 5561 to prevent the second end 5525 from passing through the first aperture 5541 during the firing stroke. Likewise, the second leg 5522 includes a first end 5524 configured to pass through the second aperture 5542 and a second end 5526 opposite the first end 5524, the second end 5526 including a second feature 5562 to prevent the second end 5526 from passing through the second aperture 5542 during the firing stroke. In one example, the first feature 5561 and second feature 5562 are each configured to engage a bottom surface of the pledget 5550 upon completion of the firing stroke, such that the pledget 5550 is driven out of the staple pocket with the first and second legs 5521, 5522.

Referring back to FIGS. 21A and 22B, the staple cartridge arrangement" described above may also include a set of arbors 6030 disposed adjacent the opening of the staple pocket, wherein the set of arbors 6030 are configured to further deform the first leg 5521 and the second leg 5522 as first leg 5521 and the second leg 5522 exit the staple pocket at the opening. FIG. 21B shows the pledget 5550 having passageways, or channels, that also act as arbors, or staple forming surfaces, as well as the additional set of arbors 6030.

A multi-part staple having a separate crown portion or pledget 5550 such as that disclosed herein also provides the benefit of the crown portion or pledget 5550 being able to act as a carrier or delivery mechanism and deliver different types of payloads to the tissue. For example, in some embodiments, the disclosed pledget 5550 may contain an absorbable foam layer or cushion that acts as a buttress layer. The foam layer or cushion may help adjust compression on the tissue by adding compliance and allowing for varying tissue thickness. In this way, a cartridge can contain one size of staple that can handle different tissue thicknesses. The absorbable foam layer may be constructed of a foam, a matrix, a cushion, an adjunct, or other elastic construct that can densify over time, including materials described in U.S. Pat. No. 10,966,722 entitled "Adjunct Materials And Methods Of Using Same In Surgical Methods For Tissue Sealing," issued Apr. 6, 2021 or adjuncts described in U.S. Pub. No. 2023/0301674 entitled "Tissue Cushion Adjunct For Surgical Stapler End Effector," published Sep. 28, 2023. In another example, rather than a foam layer, the pledget 5550 may contain and deliver a microbial or hemostatic pad, or other medicants such as antibiotics.

The staple shape and arrangement described above includes arbors and a multi-part, or deconstructed, staple with separate legs and crown pieces to facilitate staple release from the arbors. The staple crown is located above the lower arbors so that as the staple legs curl, the lower or inner arbors do not get trapped inside the staple (or the staple crown does not get trapped under the lower arbors). This avoids the issue of having to move or deploy the arbors in order to fire a staple. Thus, the disclosed staple cartridges accommodate for spanning the tissue gap and allow staple release.

The terms "upper," "lower," "vertically," "bottom," "top" or "on top," are relative terms to provide additional clarity to the figure descriptions provided below, and may refer to a position within a staple pocket. The terms "upper," "lower," "vertically," "bottom," "top" or "on top," are thus not intended to unnecessarily limit the invention described herein.

IV. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the examples below. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A staple cartridge comprising:

a set of arbors (5530) disposed adjacent a staple pocket having an opening, the set of arbors (5530) including an upper set of arbors (5531) and a lower set of arbors (5532); and a multi-part staple including a first staple leg portion (5521), a second staple leg portion (5522), and a crown portion (5550), wherein the crown portion (5550) is disposed vertically between the upper set of arbors (5531) and the lower set of arbors (5532), wherein the set of arbors (5530) are configured to curl the first staple leg portion (5521) and the second staple leg portion (5522) as the first staple leg portion (5521) and the second staple leg portion (5522) exit the staple pocket at the opening during a firing stroke.

Example 2

The staple cartridge of Example 1, wherein the crown portion (5550) includes a first aperture (5541) disposed at a first end (5561) of the crown portion (5550) and a second aperture (5542) disposed at a second end (5562) of the crown portion (5550), the first aperture (5541) being configured to receive the first staple leg portion (5521) and the second aperture (5542) being configured to receive the second staple leg portion (5522).

Example 3

The staple cartridge of Example 2, wherein a first end (5523) of the first staple leg portion (5521) and a first end (5524) of the second staple leg portion (5522) is configured to pass through the first aperture (5541) and the second aperture (5542) of the crown portion (5550), respectively, during the firing stroke.

Example 4

The staple cartridge of Example 2 or Example 3, wherein a second end (5525) of the first staple leg portion (5521) includes a feature (5560) to prevent the second end (5525) of the first staple leg portion (5521) from passing through the first aperture (5541) of the crown portion (5550) during the firing stroke, and wherein a second end (5526) of the second staple leg portion (5522) includes a feature (5560) to prevent the second end (5526) of the second staple leg portion (5522) from passing through the second aperture (5542) of the crown portion (5550) during the firing stroke, such that the crown portion (5550) releases with the first staple leg portion (5521) and the second staple leg portion (5522) into tissue upon completion of the firing stroke.

Example 5

The staple cartridge of Example 4, wherein the feature (5560) includes an out of plane bend of the second end (5525, 5526) of the first and second staple leg portions (5521, 5522).

Example 6

The staple cartridge of Example 5, wherein the out of plane bend of the second end (5525) of the first staple leg portion (5521) is in a first direction, and wherein the out of plane bend of the second end (5526) of the second staple leg portion (5522) is in a second direction opposite the first direction.

Example 7

The staple cartridge of Example 4, wherein the feature (5560) includes an end cap having a diameter larger than a diameter of the first and second apertures (5541, 5542).

Example 8

The staple cartridge of Example 4, wherein the feature (5560) includes the second end (5525, 5526) of the first and second staple leg portions (5521, 5522) having a diameter larger than a diameter of the first and second apertures (5541, 5542).

Example 9

The staple cartridge of any of Examples 1-8, wherein arbors of the upper set of arbors (5531) are spaced apart by a first distance (d1) and arbors of the lower set of arbors (5532) are spaced apart by a second distance (d2) less than the first distance (d1).

Example 10

The staple cartridge of any of Examples 1-9, wherein the crown portion (5550) is disposed on top of the lower set of arbors (5532), and wherein at least the upper set of arbors (5531) are configured to curl the first staple leg portion (5521) and the second staple leg portion (5522) as the first staple leg portion (5521) and the second staple leg portion (5522) exit the staple pocket at the opening during a firing stroke.

Example 11

The staple cartridge of any of Examples 1-10, wherein the first aperture (5541) is configured to curl the first staple leg portion (5521) as the first staple leg portion (5521) passes through the first aperture (5541) during a firing stroke, and wherein the second aperture (5542) is configured to curl the second staple leg portion (5522) as the second staple leg portion (5522) passes through the second aperture (5542) during the firing stroke.

Example 12

The staple cartridge of any of Examples 1-11, wherein the first aperture (5541) comprises a first curved passageway (6021), such that the first staple leg portion (5521) plastically deforms in a first direction as the first staple leg portion (5521) passes through the first curved passageway (6021), and wherein the second aperture (5542) comprises a second curved passageway (6022), such that the second staple leg portion (5522) plastically deforms in a second direction as the second staple leg portion (5522) passes through the second curved passageway (6022).

Example 13

The staple cartridge of Example 12, wherein the first direction and the second direction are opposite each other.

Example 14

The staple cartridge of Example 12 or Example 13, wherein the first direction is toward an arbor of the upper set of arbors (5531) closest to the first aperture (5541) and the second direction is toward an arbor of the upper set of arbors (5531) closest to the second aperture (5542).

Example 15

The staple cartridge of any of Examples 12-14, wherein the first staple leg portion (5521) and the second staple leg portion (5522) plastically deform out of plane with each other while exiting the first aperture (5541) and second aperture (5542), respectively, to form a formed staple having a three-dimensional (3D) shape.

The following clauses also relate to various non-exhaustive ways in which the teachings herein may be combined or applied.

1. A staple cartridge comprising:

a set of arbors disposed adjacent a staple pocket having an opening, the set of arbors including an upper set of arbors and a lower set of arbors; and a multi-part staple including a first staple leg portion, a second staple leg portion, and a crown portion, wherein the crown portion is disposed vertically between the upper set of arbors and the lower set of arbors, wherein the set of arbors are configured to curl the first staple leg portion and the second staple leg portion as the first staple leg portion and the second staple leg portion exit the staple pocket at the opening during a firing stroke.

2. The staple cartridge of claim 1, wherein the crown portion includes a first aperture disposed at a first end of the crown portion and a second aperture disposed at a second end of the crown portion, the first aperture being configured to receive the first staple leg portion and the second aperture being configured to receive the second staple leg portion.

3. The staple cartridge of claim 2, wherein a first end of the first staple leg portion and a first end of the second staple leg portion is configured to pass through the first aperture and the second aperture of the crown portion, respectively, during the firing stroke.

4. The staple cartridge of claim 3, wherein a second end of the first staple leg portion includes a feature to prevent the second end of the first staple leg portion from passing through the first aperture of the crown portion during the firing stroke, and wherein a second end of the second staple leg portion includes a feature to prevent the second end of the second staple leg portion from passing through the second aperture of the crown portion during the firing stroke, such that the crown portion releases with the first staple leg portion and the second staple leg portion into tissue upon completion of the firing stroke.

5. The staple cartridge of claim 4, wherein the feature includes an out of plane bend of the second end of the first and second staple leg portions.

6. The staple cartridge of claim 4, wherein the feature includes an end cap having a diameter larger than a diameter of the first and second apertures.

7. The staple cartridge of claim 1, wherein arbors of the upper set of arbors are spaced apart by a first distance and arbors of the lower set of arbors are spaced apart by a second distance less than the first distance.

8. A staple cartridge comprising:

a set of arbors disposed adjacent a staple pocket having an opening, the set of arbors including an upper set of arbors and a lower set of arbors disposed vertically below the upper set of arbors; and a multi-part staple including a first leg, a second leg, and a pledget, wherein the pledget is disposed on top of the lower set of arbors, wherein at least the upper set of arbors are configured to curl the first leg and the second leg as the first leg and the second leg exit the staple pocket at the opening during a firing stroke, wherein the pledget is configured to release with the first leg and the second leg upon completion of the firing stroke.

9. The staple cartridge of claim 8, wherein the pledget includes a first aperture disposed at a first end of the pledget and configured to receive the first leg, and a second aperture disposed at a second end of the pledget and configured to receive the second staple leg.

10. The staple cartridge of claim 9, wherein the first leg includes a first end configured to pass through the first aperture and a second end opposite the first end, the second end including a first feature to prevent the second end from passing through the first aperture during the firing stroke, and wherein the second leg includes a first end configured to pass through the second aperture and a second end opposite the first end, the second end including a second feature to prevent the second end from passing through the second aperture during the firing stroke.

11. The staple cartridge of claim 10, wherein the first feature and the second feature includes an out of plane bend of the second end of the first and second staple leg portions.

12. The staple cartridge of claim 11, wherein the out of plane bend of the second end of the first leg is in a first direction, and wherein the out of plane bend of the second end of the second leg is in a second direction opposite the first direction.

13. The staple cartridge of claim 10, wherein the first feature and the second feature includes an end cap having a diameter larger than a diameter of the first and second apertures.

14. The staple cartridge of claim 9, wherein respective first ends of respective first and second legs are configured to pass through the first and second apertures, respectively, during the firing stroke, and wherein respective second ends opposite respective first ends of respective first and second legs are configured to engage a bottom surface of the pledget upon completion of the firing stroke, such that the pledget is driven out of the staple pocket with the first and second legs.

15. A staple cartridge comprising:

a staple pocket having an opening;

a multi-part staple including a first leg, a second leg, and a pledget, wherein the pledget includes:

a first aperture disposed at a first end of the pledget and configured to receive the first leg; and a second aperture disposed at a second end of the pledget and configured to receive the second staple leg, wherein the first aperture is configured to curl the first leg as the first leg passes through the first aperture during a firing stroke, wherein the second aperture is configured to curl the second leg as the second leg passes through the second aperture during the firing stroke, and wherein the pledget is configured to release with the first leg and the second leg upon completion of the firing stroke.

16. The staple cartridge of claim 15, wherein the first aperture comprises a first curved passageway, such that the first leg plastically deforms in a first direction as the first leg passes through the first curved passageway, wherein the second aperture comprises a second curved passageway, such that the second leg plastically deforms in a second direction as the second leg passes through the second curved passageway.

17. The staple cartridge of claim 16, wherein the first direction and the second direction are opposite each other.

18. The staple cartridge of claim 15, wherein the first leg includes a first end configured to pass through the first aperture and a second end opposite the first end, the second end including a first feature to prevent the second end from passing through the first aperture during the firing stroke, and wherein the second leg includes a first end configured to pass through the second aperture and a second end opposite the first end, the second end including a second feature to prevent the second end from passing through the second aperture during the firing stroke.

19. The staple cartridge of claim 18, wherein the first feature and second feature are each configured to engage a bottom surface of the pledget upon completion of the firing stroke, such that the pledget is driven out of the staple pocket with the first and second legs.

20. The staple cartridge of claim 15, further comprising a set of arbors disposed adjacent the opening of the staple pocket, wherein the set of arbors are configured to deform the first leg and the second leg as first leg and the second leg exit the staple pocket at the opening.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Patent Application Ser. No. 63/467,622, entitled "Surgical Stapler Cartridge Having Intermediate Raised Tissue Engagement Protrusions," filed on May 19, 2023; U.S. Patent Application Ser. No. 63/467,623, entitled "Surgical Stapler Cartridge Having Tissue Engagement Protrusions with Enlarged Engagement Surface," filed on May 19, 2023; U.S. Patent Application Ser. No. 63/467,648, entitled "Surgical Stapler Cartridge Having Raised Surface to Promote Buttress Adhesion," filed on May 19, 2023; U.S. Patent Application Ser. No. 63/467,469, entitled "Surgical Stapler Cartridge Having Cartridge Retention Features," filed on May 19, 2023; U.S. Patent Application Ser. No. 63/459,739, entitled "Surgical Stapler Anvil Having Staple Forming Pockets with Laterally Varying Orientations," filed on May 19, 2023; U.S. Patent Application Ser. No. 63/467,656, entitled "Surgical Stapler With Discretely Positionable Distal Tip," filed on May 19, 2023; and/or U.S. Patent Application Ser. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Patent Application Ser. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A staple cartridge comprising:
a set of arbors disposed adjacent a staple pocket having an opening, the set of arbors including an upper set of arbors and a lower set of arbors; and
a multi-part staple including a first staple leg portion, a second staple leg portion, and a crown portion, wherein the crown portion is disposed vertically between the upper set of arbors and the lower set of arbors,
wherein the set of arbors are configured to curl the first staple leg portion and the second staple leg portion as the first staple leg portion and the second staple leg portion exit the staple pocket at the opening during a firing stroke.

2. The staple cartridge of claim 1, wherein the crown portion includes a first aperture disposed at a first end of the crown portion and a second aperture disposed at a second end of the crown portion, the first aperture being configured to receive the first staple leg portion and the second aperture being configured to receive the second staple leg portion.

3. The staple cartridge of claim 2, wherein a first end of the first staple leg portion and a first end of the second staple leg portion is configured to pass through the first aperture and the second aperture of the crown portion, respectively, during the firing stroke.

4. The staple cartridge of claim 3,
wherein a second end of the first staple leg portion includes a feature to prevent the second end of the first staple leg portion from passing through the first aperture of the crown portion during the firing stroke, and
wherein a second end of the second staple leg portion includes a feature to prevent the second end of the second staple leg portion from passing through the second aperture of the crown portion during the firing stroke,
such that the crown portion releases with the first staple leg portion and the second staple leg portion into tissue upon completion of the firing stroke.

5. The staple cartridge of claim 4, wherein the feature includes an out of plane bend of the second end of the first and second staple leg portions.

6. The staple cartridge of claim 4, wherein the feature includes an end cap having a diameter larger than a diameter of the first and second apertures.

7. The staple cartridge of claim 1, wherein arbors of the upper set of arbors are spaced apart by a first distance and arbors of the lower set of arbors are spaced apart by a second distance less than the first distance.

8. A staple cartridge comprising:
a set of arbors disposed adjacent a staple pocket having an opening, the set of arbors including an upper set of arbors and a lower set of arbors disposed vertically below the upper set of arbors; and
a multi-part staple including a first leg, a second leg, and a pledget, wherein the pledget is disposed on top of the lower set of arbors,
wherein at least the upper set of arbors are configured to curl the first leg and the second leg as the first leg and the second leg exit the staple pocket at the opening during a firing stroke,
wherein the pledget is configured to release with the first leg and the second leg upon completion of the firing stroke.

9. The staple cartridge of claim 8, wherein the pledget includes
a first aperture disposed at a first end of the pledget and configured to receive the first leg, and
a second aperture disposed at a second end of the pledget and configured to receive the second staple leg.

10. The staple cartridge of claim 9,
wherein the first leg includes a first end configured to pass through the first aperture and a second end opposite the first end, the second end including a first feature to prevent the second end from passing through the first aperture during the firing stroke, and
wherein the second leg includes a first end configured to pass through the second aperture and a second end opposite the first end, the second end including a second feature to prevent the second end from passing through the second aperture during the firing stroke.

11. The staple cartridge of claim 10, wherein the first feature and the second feature includes an out of plane bend of the second end of the first and second staple leg portions.

12. The staple cartridge of claim 11, wherein the out of plane bend of the second end of the first leg is in a first direction, and wherein the out of plane bend of the second end of the second leg is in a second direction opposite the first direction.

13. The staple cartridge of claim 10, wherein the first feature and the second feature includes an end cap having a diameter larger than a diameter of the first and second apertures.

14. The staple cartridge of claim 9, wherein respective first ends of respective first and second legs are configured to pass through the first and second apertures, respectively, during the firing stroke, and wherein respective second ends opposite respective first ends of respective first and second legs are configured to engage a bottom surface of the pledget upon completion of the firing stroke, such that the pledget is driven out of the staple pocket with the first and second legs.

15. A staple cartridge comprising:
a staple pocket having an opening;
a multi-part staple including a first leg, a second leg, and a pledget, wherein the pledget includes:
a first aperture disposed at a first end of the pledget and configured to receive the first leg; and
a second aperture disposed at a second end of the pledget and configured to receive the second staple leg,
wherein the first aperture is configured to curl the first leg as the first leg passes through the first aperture during a firing stroke,
wherein the second aperture is configured to curl the second leg as the second leg passes through the second aperture during the firing stroke, and
wherein the pledget is configured to release with the first leg and the second leg upon completion of the firing stroke.

16. The staple cartridge of claim 15,
wherein the first aperture comprises a first curved passageway, such that the first leg plastically deforms in a first direction as the first leg passes through the first curved passageway,
wherein the second aperture comprises a second curved passageway, such that the second leg plastically deforms in a second direction as the second leg passes through the second curved passageway.

17. The staple cartridge of claim 16, wherein the first direction and the second direction are opposite each other.

18. The staple cartridge of claim 15,
wherein the first leg includes a first end configured to pass through the first aperture and a second end opposite the first end, the second end including a first feature to prevent the second end from passing through the first aperture during the firing stroke, and wherein the second leg includes a first end configured to pass through the second aperture and a second end opposite the first end, the second end including a second feature to prevent the second end from passing through the second aperture during the firing stroke.

19. The staple cartridge of claim 18, wherein the first feature and second feature are each configured to engage a bottom surface of the pledget upon completion of the firing stroke, such that the pledget is driven out of the staple pocket with the first and second legs.

20. The staple cartridge of claim 15, further comprising a set of arbors disposed adjacent the opening of the staple pocket, wherein the set of arbors are configured to deform the first leg and the second leg as first leg and the second leg exit the staple pocket at the opening.

* * * * *